United States Patent
Babb et al.

(10) Patent No.: US 6,627,573 B2
(45) Date of Patent: Sep. 30, 2003

(54) EXPANDED ANIONIC COMPOUNDS COMPRISING HYDROXYL OR QUIESCENT REACTIVE FUNCTIONALITY AND CATALYST ACTIVATORS THEREFROM

(75) Inventors: David A. Babb, Lake Jackson, TX (US); Richard E. Campbell, Jr., Midland, MI (US); David R. Neithamer, Midland, MI (US); Grant B. Jacobsen, Houston, TX (US); Edmund M. Carnahan, Fresno, TX (US)

(73) Assignee: The Dow Chemical Company, Midland, MI (US)

( * ) Notice: Subject to any disclaimer, the term of this patent is extended or adjusted under 35 U.S.C. 154(b) by 0 days.

(21) Appl. No.: 09/904,422

(22) Filed: Jul. 12, 2001

(65) Prior Publication Data

US 2002/0032120 A1 Mar. 14, 2002

Related U.S. Application Data

(60) Provisional application No. 60/219,496, filed on Jul. 20, 2000.

(51) Int. Cl.[7] ................................................ B01J 30/00
(52) U.S. Cl. ................ 502/150; 502/164; 502/202; 502/414; 526/134; 548/101; 548/110
(58) Field of Search ................. 502/150, 164, 502/202, 414; 526/134; 548/101, 110

(56) References Cited

U.S. PATENT DOCUMENTS

| | | |
|---|---|---|
| 4,522,987 A | 6/1985 | Hogan et al. |
| 4,543,399 A | 9/1985 | Jenkens, III et al. |
| 4,564,647 A | 1/1986 | Hayashi et al. |
| 4,588,790 A | 5/1986 | Jenkens, III et al. |
| 5,032,652 A | 7/1991 | Chang |
| 5,084,534 A | 1/1992 | Welborn, Jr. et al. |
| 5,132,380 A | 7/1992 | Stevens et al. |
| 5,153,157 A | 10/1992 | Hlatky et al. |
| 5,189,192 A | 2/1993 | LaPointe et al. |
| 5,198,401 A | 3/1993 | Turner et al. |
| 5,321,106 A | 6/1994 | LaPointe |
| 5,350,723 A | 9/1994 | Neithamer et al. |
| 5,352,749 A | 10/1994 | DeChellis et al. |
| 5,405,922 A | 4/1995 | DeChellis et al. |
| 5,407,884 A | 4/1995 | Turner et al. |
| 5,447,895 A | 9/1995 | Marks et al. |
| 5,470,927 A | 11/1995 | Turner et al. |
| 5,625,087 A | 4/1997 | Devore et al. |
| 6,087,293 A | 7/2000 | Carnahan et al. |
| 6,395,671 B2 * | 5/2002 | LaPointe ............... 502/150 |

FOREIGN PATENT DOCUMENTS

| | | |
|---|---|---|
| EP | 0 089 691 A2 | 9/1983 |
| EP | 448240 A2 | 9/1991 |
| EP | 520732 | 12/1992 |
| EP | 924223 A2 | 6/1999 |
| WO | WO 88/02009 A1 | 3/1988 |
| WO | WO 94/00500 A1 | 1/1994 |
| WO | WO 94/25495 A1 | 11/1994 |
| WO | WO 94/28032 A1 | 12/1994 |
| WO | WO 99/15534 A1 | 4/1999 |
| WO | WO 99/42467 A1 | 8/1999 |
| WO | WO 00/20426 A1 | 4/2000 |
| WO | WO 01/09207 A2 | 2/2001 |

OTHER PUBLICATIONS

Marks, et al., J. Am. Chem. Soc., 118, 12451–12452 (1996).
PCT International Search Report, Dec. 6, 2001.
Robert E. LaPointe et al., New Family of Weakly Coordinating Anions, *J. Am. Chem. Soc.* 2000, Sep. 16, 2000, pp. 9560–9561, vol. 122(39).
Marco Lucarini et al., An EPR Study of the Reaction of Tetrabutylammonium borohydride with N–Heterocycles, *J. Organomet. Chem*, 1995, pp. 123–131, vol. 494 (1–2).

* cited by examiner

*Primary Examiner*—Joseph K. McKane
*Assistant Examiner*—Kamal Saeed

(57) ABSTRACT

A compound useful as a cocatalyst or cocatalyst component, especially for use as an addition polymerization catalyst compound, corresponding to the formula:

$$(A^{*+a})_b(Z^*J^*_j)^{-c}_d,$$

wherein:

A* is a cation of from 1 to 80, preferably 1 to 60 atoms, not counting hydrogen atoms, said A* having a charge +a, Z* is an anion group of from 1 to 50, preferably 1 to 30 atoms, not counting hydrogen atoms, further containing two or more Lewis base sites;

J* independently each occurrence is a Lewis acid of from 1 to 80, preferably 1 to 60 atoms, not counting hydrogen atoms, coordinated to at least one Lewis base site of Z*, and optionally two or more such J* groups may be joined together in a moiety having multiple Lewis acidic functionality, j is a number from 2 to 12 and a, b, c, and d are integers from 1 to 3, with the proviso that a×b is equal to c×d, and provided further that one or more of A*, Z* or J* comprises a hydroxyl group or a polar group containing quiescent reactive functionality.

10 Claims, No Drawings

EXPANDED ANIONIC COMPOUNDS COMPRISING HYDROXYL OR QUIESCENT REACTIVE FUNCTIONALITY AND CATALYST ACTIVATORS THEREFROM

CROSS REFERENCE STATEMENT

This application claims the benefit of U.S. Provisional Application No. 60/219,496, filed Jul. 20, 2000.

BACKGROUND INFORMATION

The present invention relates to compounds that are useful as catalyst components. More particularly the present invention relates to such compounds that are particularly adapted for use in the coordination polymerization of unsaturated compounds comprising an anion containing at least two Lewis basic sites which are coordinated to Lewis acids, and further containing a hydroxyl group or a polar group containing a quiescent reactive functionality. Such compounds are particularly advantageous for use in forming supported polymerization catalysts wherein at least the catalyst activator is chemically attached to a substrate material.

It is previously known in the art to activate Ziegler-Natta polymerization catalysts, particularly such catalysts comprising Group 3–10 metal complexes containing delocalized π-bonded ligand groups, by the use of Bronsted acid salts capable of transferring a proton to form a cationic derivative or other catalytically active derivative of such Group 3–10 metal complex. Preferred Bronsted acid salts are such compounds containing a cation/anion pair that is capable of rendering the Group 3–10 metal complex catalytically active. Suitable activators comprise fluorinated arylborate anions, such as tetrakis(pentafluorophenyl)borate. Additional suitable anions include sterically shielded diboron anions of the formula:

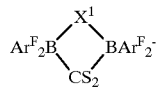

wherein:
S is hydrogen, alkyl, fluoroalkyl, aryl, or fluoroaryl, $Ar^F$ is fluoroaryl, and $X^1$ is either hydrogen or halide, disclosed in U.S. Pat. No. 5,447,895. Additional examples include carborane compounds such as are disclosed and claimed in U.S. Pat. No. 5,407,884.

Examples of preferred charge separated (cation/anion pair) activators are ammonium, sulfonium, or phosphonium salts capable of transferring a hydrogen ion, disclosed in U.S. Pat. No. 5,198,401, U.S. Pat. No. 5,132,380, U.S. Pat. No. 5,470,927 and U.S. Pat. No. 5,153,157, as well as oxidizing salts such as ferrocenium, silver or lead salts, disclosed in U.S. Pat. No. 5,189,192 and U.S. Pat. No. 5,321,106 and strongly Lewis acidic salts such as carbonium or silylium salts, disclosed in U.S. Pat. No. 5,350,723 and U.S. Pat. No. 5,625,087.

Further suitable activators for the above metal complexes include strong Lewis acids including tris(perfluorophenyl)borane and tris(perfluorobiphenyl)borane. The former composition has been previously disclosed for the above stated end use in EP-A-520,732, whereas the latter composition is similarly disclosed by Marks, et al., in *J. Am. Chem. Soc.*, 118, 12451–12452 (1996).

Despite the satisfactory performance of the foregoing catalyst activators under a variety of polymerization conditions, there is still a need for improved cocatalysts for use in the activation of various metal complexes especially under a variety of reaction conditions. Accordingly, it would be desirable if there were provided compounds that could be employed in solution, slurry, gas phase or high pressure polymerizations and under homogeneous or heterogeneous process conditions having improved activation properties. In particular, it would be desirable to provide compounds that may be chemically bonded to support materials to prepare supported catalyst components having improved resistance to solvent removal and loss from the particle surface.

SUMMARY OF THE INVENTION

According to the present invention there are now provided compounds useful as catalyst activators corresponding to the formula:

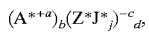

wherein:
A* is a cation of from 1 to 80, preferably 1 to 60 atoms, not counting hydrogen atoms, said A* having a charge +a, Z* is an anion group of from 1 to 50, preferably 1 to 30 atoms, not counting hydrogen atoms, further containing two or more Lewis base sites;

J* independently each occurrence is a Lewis acid of from 1 to 80, preferably 1 to 60 atoms, not counting hydrogen atoms, coordinated to at least one Lewis base site of Z*, and optionally two or more such J* groups may be joined together in a moiety having multiple Lewis acidic functionality, j is a number from 2 to 12 and a, b, c, and d are integers from 1 to 3, with the proviso that a×b is equal to c×d, and provided further that one or more of A*, Z* or J* comprises a hydroxyl group or a polar group containing quiescent reactive functionality.

The foregoing compounds, in particular, those containing quiescent reactive functionality may be utilized in combination with one or more Group 3–10 or Lanthanide metal complexes to form catalyst compositions for polymerization of addition polymerizable monomers, especially ethylenically unsaturated monomers, most preferably, $C_{2-20,000}$ α-olefins. Additionally, the compounds may be utilized to form latent activators, that is, compounds that may themselves not cause a metal complex to become catalytically active, but which may be converted to such a compound, by, for example, in-situ reaction of the hydroxyl group or quiescent reactive functionality or its derivative with a Lewis acid, especially an aluminum hydrocarbyl compound, or an alkali metal halide or ammonium halide salt. Moreover, the compounds may be deposited onto solid supports, such as by impregnation, surface deposition, physisorption or chemical reaction with the support, reactive functionality of the support, or chemical modifiers associated with the support, to form heterogeneous catalyst components for use in preparing heterogeneous catalyst compositions for use in polymerization of the foregoing monomers.

In one embodiment of the invention, the foregoing compounds are used to form supported catalyst components by reaction of the hydroxyl group thereof with reactive functionality of a support material, or by conversion of the quiescent reactive functionality to a reactive functionality and reaction thereof with reactive functionality of a support material. The resulting supported catalyst components are highly resistant to loss of activator compound in a liquid reaction medium such as occurs in a slurry polymerization.

One or more Group 3–10 or Lanthanide metal complexes, preferably a Group 4 metal complex, and additional additives, modifiers and adjuvants may be added to the catalyst component, either before, after or simultaneous with addition of the cocatalyst of the present invention, to form the fully formulated catalyst composition.

Additionally according to the present invention there is provided a catalyst composition for polymerization of an ethylenically unsaturated, polymerizable monomer comprising, in combination, the above described activated derivative compound, a Group 3–10 metal complex that is capable of activation to form an addition polymerization catalyst, or the reaction product of such combination, and optionally a support.

Additionally according to the present invention there is provided a process for polymerization of one or more ethylenically unsaturated, polymerizable monomers comprising contacting the same, optionally in the presence of an inert aliphatic, alicyclic or aromatic hydrocarbon, with the above catalyst composition or supported catalyst composition.

The foregoing compounds are uniquely adapted for use in activation of a variety of metal complexes, especially Group 4 metal complexes, under standard and atypical olefin polymerization conditions. Because of this fact, the foregoing compounds are capable of forming highly desirable olefin polymers in high efficiency.

DETAILED DESCRIPTION OF THE INVENTION

All references herein to elements belonging to a certain Group refer to the Periodic Table of the Elements published and copyrighted by CRC Press, Inc., 1995. Also any reference to the Group or Groups shall be to the Group or Groups as reflected in this Periodic Table of the Elements using the IUPAC system for numbering groups. When referred to herein, the teachings of any patent, patent application or publication are hereby incorporated by reference herein.

The catalyst activators of the invention are further characterized in the following manner. $A^{*+a}$ is desirably chosen to provide overall neutrality to the compound and to not interfere with subsequent catalytic activity. Moreover, the cation may participate in the formation of the active catalyst species, desirably through a proton transfer, oxidation, or ligand abstraction mechanism, or a combination thereof. Additionally, certain cations beneficially improve the solubility of the resulting activator in particular reaction media under use conditions. For example, in the homopolymerization or copolymerization of aliphatic olefins, particularly in the solution phase, an aliphatic diluent is commonly used. Accordingly, cationic species that are relatively soluble in such reaction media, or render the catalyst activator more soluble therein are highly preferred.

Examples of suitable cations include ammonium, sulfonium, phosphonium, oxonium, carbonium, and silylium cations, preferably those containing up to 80 atoms not counting hydrogen, as well as ferrocenium, $Ag^+$, $Pb^{+2}$, or similar oxidizing cations. As previously mentioned, the cation may also comprise a hydroxyl group or a polar group containing quiescent reactive functionality. In a preferred embodiment, a, b, c and d are all equal to one.

Z* can be any anionic moiety containing two or more Lewis basic sites. Preferably, the Lewis base sites are on different atoms of a polyatomic anionic moiety. Desirably, such Lewis basic sites are relatively sterically accessible to the Lewis acid, J*. Preferably the Lewis basic sites are on nitrogen or carbon atoms. Examples of suitable Z* anions include cyanide, azide, amide and substituted amide, amidinide and substituted amidinide, dicyanamide, imidazolide, substituted imidazolide, imidazolinide, substituted imidazolinide, tricyanomethide, tetracycanoborate, puride, squarate, 1,2,3-triazolide, substituted 1,2,3-triazolide, 1,2,4-triazolide, substituted 1,2,4-triazolide, pyrimidinide, substituted pyrimidinide, tetraimidazoylborate and substituted tetraimidazoylborate anions, wherein each group, if present, is a halo-, hydrocarbyl-, halohydrocarbyl-, silyl-, (including mono-, di- and tri(hydrocarbyl)silyl-), silylhydrocarbyl-, halocarbyl- or hydroxyl-group, or a polar group containing quiescent reactive functionality, or two such groups together form a saturated or unsaturated ring- or multiple ring-system.

Preferred Z* groups are: imidazolide, 2-nonadecylimidazolide, 2-undecylimidazolide, 2-tridecylimidazolide, 2-pentadecylimidazolide, 2-heptadecylimidazolide, 2-nonadecylimidazolide, 4,5-difluoroimidazolide, 4,5-dichloroimidazolide, 4,5-dibromoimidazolide, 4,5-bis(heptadecyl)imidazolide, 4,5-bis(undecyl)imidazolide, imidazolinide, 2-nonadecylimidazolinide, 2-undecylimidazolinide, 2-tridecylimidazolinide, 2-pentadecylimidazolinide, 2-heptadecylimidazolinide, 2-nonadecylimidazolinide, 4,5-difluoroimidazolinide, 4,5-dichloroimidazolinide, 4,5-dibromoimidazolinide, 4,5-bis(heptadecyl)imidazolinide, 4,5-bis(undecyl)imidazolinide, didecylamide, piperidinide, 4,4-dimethylimidazolinide, tetra-5-pyrimidinylborate, pyrimidinide, 5,6-dichlorobenzimidazolide, 4,5-dicyanoimidazolide, and 5,6-dimethylbenzimidazolide anions, or said Z* groups that are further substituted with a hydroxyl group or a polar group containing quiescent reactive functionality.

Coordinated to the Lewis base sites of the anion are from 2 to 12 Lewis acids, J*, two or more of which may be joined together in a moiety having multiple Lewis acidic functionality. Optionally, said J* group may comprise a hydroxyl group or a polar group containing quiescent reactive functionality, so long as such functionality does not interfere with the Lewis acid functionality of the group. Preferably, from 2 to 4 J* groups having from 3 to 100 atoms not counting hydrogen are present.

More specific examples of the foregoing Lewis acid compounds, J*, correspond to the formula:

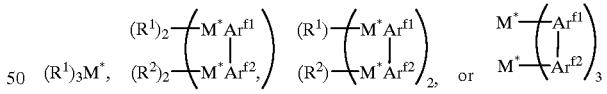

wherein:
M* is aluminum, gallium or boron;
$R^1$ and $R^2$ independently each occurrence are hydride, halide, or a hydrocarbyl, halocarbyl, halohydrocarbyl, dialkylamido, alkoxide, or aryloxide group of up to 20 carbons, optionally substituted with a hydroxyl group or a polar group containing quiescent reactive functionality, and
$Ar^{f1}$–$Ar^{f2}$ in combination, independently each occurrence, is a divalent fluoro-substituted aromatic group of from 6 to 20 carbons, optionally substituted with a hydroxyl group or a polar group containing quiescent reactive functionality.

Highly preferred Lewis acids are aluminum or boron compounds corresponding to the formula: $AlR^1_3$, or $BR^1_3$, wherein $R^1$ independently each occurrence is selected from hydrocarbyl, halocarbyl, and halohydrocarbyl radicals, or such groups further substituted with a hydroxyl group or a polar group containing quiescent reactive functionality, said $R^1$ having up to 20 carbons. In a more highly preferred embodiment, $R^1$ is a fluorinated $C_{1-20}$ hydrocarbyl group, most preferably, a fluorinated aryl group, especially, pentafluorophenyl.

Preferred examples of the foregoing Lewis acid groups containing multiple Lewis acid sites are:

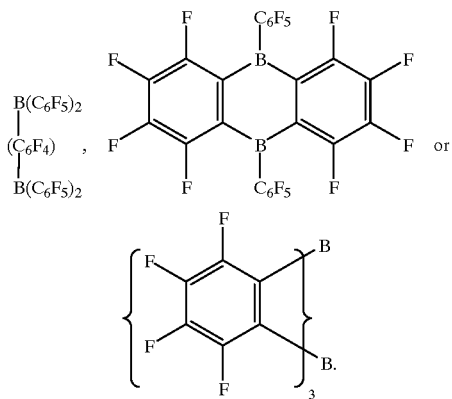

By the term "polar group containing quiescent reactive functionality" is meant an oxygen, nitrogen, sulfur, or phosphorus containing ligand group that is capped or protected and thereby rendered relatively inert to reaction conditions used in the synthesis or use of the present compounds, but wherein the capping or protecting groups may be later removed, if desired, thereby generating a reactive polar functional group, especially a hydroxyl group or metallated derivative thereof. Suitable reactive polar functional groups include hydroxyl, thiol, amine, and phosphine groups, or hydrocarbyl-, alkali metal- or Bronsted acid salt-derivatives thereof. Suitable quiescent reactive functionality includes the trihydrocarbyllsilyl-, trihydrocarbylgermyl-, dihydrocarbylaluminum-, hydrocarbylzinc- or hydrocarbylmagnesium-functionalized derivative of the foregoing polar groups. Particularly preferred polar containing quiescent reactive functional groups are trihydrocarbylsiloxy, trihydrocarbylsiloxy-substituted hydrocarbyl, dihydrocarbylaluminoxy and dihydrocarbylaluminoxy substituted hydrocarbyl groups. Especially preferred are the trialkylsiloxy- or dialkylaluminoxy-derivatives of such polar functional groups, containing from 1 to 6 carbon in each alkyl group. Especially preferred quiescent reactive functional groups are trimethylsiloxy-groups and diethylaluminoxy-groups.

Such polar group containing quiescent reactive functionality is activated by reaction with a metal hydrocarbyl-, metal halocarbyl-, hydrocarbylmetaloxy- or metal halohydrodarbyl-compound under ligand exchange conditions, thereby producing a neutral hydrocarbon, halohydrocarbon, trimethylsilylhydrocarbon, trimethylsilylhalohydrocarbon or trimethylsilylhalocarbon compound as a by-product. The hydroxyl group or polar group containing quiescent reactive functionality may also be employed to react with hydroxyl-, alkylmetal-, hydrocarbylsilyl-, or hydrocarbylsiloxy-functionality of a solid, particulated, support material, optionally after conversion to a metallated or protonated intermediate. This results in tethering or chemically attaching the activator to the surface of the solid, particulated, support material. The resulting substance demonstrates enhanced resistance to loss or removal when exposed to liquids in a polymerization process.

In a preferred embodiment, the foregoing hydroxyl group or polar group containing quiescent reactive functionality is located in the Z* ligand. Examples include hydroxyl, trialkylsiloxy-, trialkylsiloxyalkyl-, trialkylsiloxyaryl-, and dialkylaluminoxyaryl-substituted derivatives of imidazolide, 2-($C_{1-30}$hydrocarbyl)imidazolide, 4,5-dihaloimidazolide, 4,5-di($C_{1-30}$hydrocarbyl)imidazolide, 4,5-benzylimidazolide, 2-($C_{1-30}$hydrocarbyl)-4,5-benzimidazolide, 1,3,4-triazolide, 2-($C_{1-30}$hydrocarbyl-1,3,4-triazolide, 1,2,3-triazolide, 4,5-benz-1,2,3-triazolide, imidazolinide, 2-($C_{1-30}$hydrocarbyl)imidazolinide, 4,5-dihaloimidazolinide, and 5,6-dimethylbenzimidazolide. Especially preferred examples include hydroxyaryl, trimethylsiloxyaryl-, and dialkylaluminoxyaryl-substituted derivatives of imidazolide, 2-($C_{1-30}$alkyl)imidazolide, 4,5-di($C_{1-30}$alkyl)imidazolide, 4,5-benzimidazolide, 1,3,4-triazolide, 2-($C_{1-30}$alkyl-1,3,4-triazolide, and 1,2,3-triazolide.

Especially suitable expanded anion compounds according to the present invention include the ammonium, phosphonium, sulfonium, oxonium, carbonium, silylium, lead (II), silver or ferrocenium salts of hydroxylphenyl-, trimethylsiloxyphenyl-, and dialkylaluminoxyphenyl-substituted derivatives of: bis(tris(pentafluorophenyl)borane)imidazolide, bis(tris(pentafluorophenyl)borane)-2-undecyl-imidazolide, bis(tris(pentafluorophenyl)borane) imidazolinide, bis(tris(pentafluorophenyl)-borane)-2-undecylimidazolinide, bis(tris(pentafluorophenyl)borane)-4,5-benzimidazolide, bis(tris(pentafluorophenyl)borane)-4,5-bis(heptadecyl)imidazolide, bis(tris(pentafluorophenyl) borane)1,3,4-triazolide, bis(tris(pentafluorophenyl)borane)-2-undecyl-1,3,4-triazolide, bis(tris(pentafluorophenyl) alumane)imidazolide, bis(tris(pentafluorophenyl)alumane)-2-undecylimidazolide, bis(tris(pentafluorophenyl)alumane) imidazolinide, bis(tris(pentafluorophenyl)alumane)-2-undecylimidazolinide, bis(tris-(pentafluorophenyl) alumane)-4,5-benzimidazolide, bis(tris(pentafluoro-phenyl) alumane)-4,5-bis(heptadecyl)imidazolide, bis(tris (pentafluorophenyl)alumane)-1,3,4-triazolide, and bis(tris (pentafluorophenyl)alumane)-2-undecyl-1,3,4-triazolide.

Preferred expanded anion compounds are the ammonium salts of the foregoing derivatives, especially those which comprise trihydrocarbyl-substituted ammonium cations, especially trimethylammonium-, triethylammonium-, tripropylammonium-, tri(n-butyl)ammonium-, methyldi(octadecyl)ammonium-, methyldi(tetradecyl)ammonium-, methyl(tetradecyl) (octadecyl)ammonium-, N,N-dimethylanilinium-, N,N-diethylanilinium-, N,N-dimethyl (2,4,6-trimethylanilinium)-, N,N-di(tetradecyl)anilinium-, N,N-di(tetradecyl)-2,4,6-trimethylanilinium)-, N,N-di (octadecyl)lanilinium-, N,N-di(octadecyl)-2,4,6-trimethylanilinium)-, and methyldicyclohexylammonium-cations, or mixtures thereof.

Most preferred ammonium cation containing salts are those containing trihydrocarbyl-substituted ammonium cations containing one or two $C_{10}$–$C_{40}$ alkyl groups, especially methylbis(octadecyl)ammonium- and methylbis(tetradecyl) ammonium-cations. It is further understood that the cation may comprise a mixture of hydrocarbyl groups of differing lengths. For example, the protonated ammonium cation derived from the commercially available long chain amine comprising a mixture of two $C_{14}$, $C_{16}$ or $C_{18}$ alkyl groups and one methyl group. Such amines are available from Witco Corp., under the trade name Kemamine™ T9701, and from Akzo-Nobel under the trade name Armeen™ M2HT.

The foregoing cocatalysts (illustrated by those having substituted-imidazolide, imidazolinide, benzimidazolide, 1,3,4-triazolide, 1,2,3-triazolide, or 4,5-benzyl-1,2,3-triazolide anions containing one or more hydroxyl-, trimethylsiloxy-, trimethylsiloxyalkyl-, or trimethylsiloxyaryl-groups) may be depicted schematically as follows:

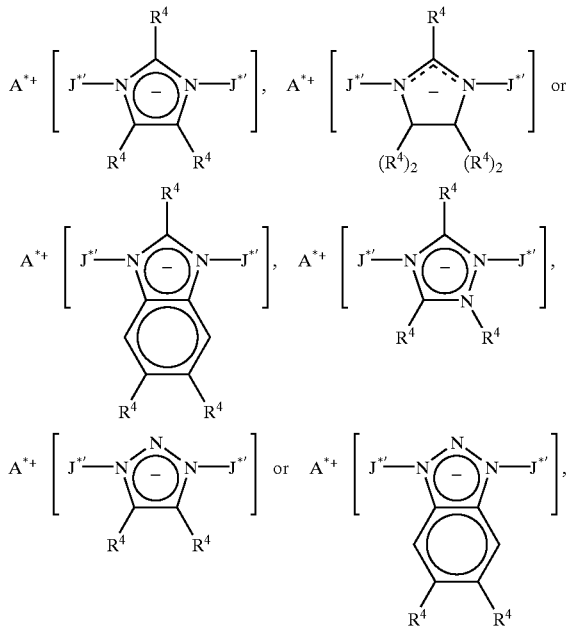

wherein:
- $A^{*+}$ is a monovalent cation as previously defined, and preferably is a trihydrocarbyl ammonium cation, containing one or two $C_{10-40}$ alkyl groups, especially the methylbis(tetradecyl)ammonium- or methylbis(octadecyl)ammonium-cation,
- $R^4$, independently each occurrence, is hydrogen or a hydroxyhydrocarbyl, halo, hydrocarbyl, halocarbyl, halohydrocarbyl, silylhydrocarbyl, or silyl group, (including mono-, di- and tri(hydrocarbyl)silyl) group of up to 30 atoms not counting hydrogen, preferably $C_{1-20}$ alkyl group, or a quiescent reactive group, with the proviso that at least one $R^4$ group contains a hydroxyhydrocarbyl group or a quiescent reactive group, preferably a hydroxyaryl, trialkylsiloxy-, trialkylsiloxyalkyl-, trialkylsiloxyaryl-, or dialkyllaluminoxyaryl-ligand, more preferably a trimethylsiloxy-, trimethylsiloxymethyl-, trimethylsiloxyphenyl-, or diethylaluminoxyphenyl-ligand, and
- $J^{*\prime}$ is tris(pentafluorophenyl)borane or tris(pentafluorophenyl)alumane).

Examples of the most highly preferred catalyst activators herein include the forgoing trihydrocarbylammonium-, especially, methylbis(tetradecyl)ammonium- or methylbis(octadecyl)ammonium-salts of:

bis(tris(pentafluorophenyl)borane)-2-(p-hydroxyphenyl)imidazolide,
bis(tris(pentafluorophenyl)borane)-2-(p-hydroxybiphenyl)imidazolide,
bis(tris(pentafluorophenyl)borane)-5-(p-hydroxynaphthyl)imidazolide,
bis(tris(pentafluorophenyl)borane)-2-undecyl-4-(p-hydroxyphenyl)imidazolide,
bis(tris(pentafluorophenyl)borane)-2-heptadecyl-4-(p-hydroxyphenyl)imidazolide,
bis(tris(pentafluorophenyl)borane)-2-(p-hydroxyphenyl)-4,5-bis(undecyl)imidazolide,
bis(tris(pentafluorophenyl)borane)-2-(p-hydroxyphenyl)-4,5-bis(heptadecyl)imidazolide,
bis(tris(pentafluorophenyl)borane)-2-(p-hydroxyphenyl)imidazolinide,
bis(tris(pentafluorophenyl)borane)-2-(p-hydroxyphenyl)-1,3,4-triazolide,
bis(tris(pentafluorophenyl)borane)-2-(p-hydroxyphenyl)-4,5-benziimidazolide;
bis(tris(pentafluorophenyl)borane)-2-(p-trimethylsiloxyphenyl)imidazolide,
bis(tris(pentafluorophenyl)borane)-2-undecyl-4-(p-trimethylsiloxyphenyl)imidazolide,
bis(tris(pentafluorophenyl)borane)-2-heptadecyl-4-(p-trimethylsiloxyphenyl)imidazolide,
bis(tris(pentafluorophenyl)borane)-2-(p-trimethylsiloxyphenyl)-4,5-bis(undecyl)imidazolide,
bis(tris(pentafluorophenyl)borane)-2-(p-trimethylsiloxyphenyl)-4,5-bis(heptadecyl)imidazolide,
bis(tris(pentafluorophenyl)borane)-2-(p-trimethylsiloxyphenyl)imidazolinide,
bis(tris(pentafluorophenyl)borane)-2-(p-trimethylsiloxyphenyl)-1,3,4-triazolide,
bis(tris(pentafluorophenyl)borane)-2-(p-trimethylsiloxyphenyl)-4,5-benziimidazolide;
bis(tris(pentafluorophenyl)borane)-2-(p-diethylaluminoxyphenyl)imidazolide,
bis(tris(pentafluorophenyl)borane)-2-(p-diethylaluminoxybiphenyl)imidazolide,
bis(tris(pentafluorophenyl)borane)-5-(p-diethylaluminoxynaphthyl)imidazolide,
bis(tris(pentafluorophenyl)borane)-2-undecyl-4-(p-diethylaluminoxyphenyl)imidazolide,
bis(tris(pentafluorophenyl)borane)-2-heptadecyl-4-(p-diethylaluminoxyphenyl)imidazolide,
bis(tris(pentafluorophenyl)borane)-2-(p-diethylaluminoxyphenyl)-4,5-bis(undecyl)imidazolide,
bis(tris(pentafluorophenyl)borane)-2-(p-diethylaluminoxyphenyl)-4,5-bis(heptadecyl)imidazolide,
bis(tris(pentafluorophenyl)borane)-2-(p-diethylaluminoxyphenyl)imidazolinide,
bis(tris(pentafluorophenyl)borane)-2-(p-diethylaluminoxyphenyl)-1,3,4-triazolide,
bis(tris(pentafluorophenyl)borane)-2-(p-diethylaluminoxyphenyl)-4,5-benziimidazolide;
bis(tris(pentafluorophenyl)alumane)-2-(p-hydroxyphenyl)imidazolide,
bis(tris(pentafluorophenyl)alumane)-2-undecyl-4-(p-hydroxyphenyl)imidazolide,
bis(tris(pentafluorophenyl)alumane)-2-heptadecyl-4-(p-hydroxyphenyl)imidazolide,
bis(tris(pentafluorophenyl)alumane)-2-(p-hydroxyphenyl)-4,5-bis(undecyl)imidazolide,
bis(tris(pentafluorophenyl)alumane)-2-(p-hydroxyphenyl)-4,5-bis(heptadecyl)imidazolide,
bis(tris(pentafluorophenyl)alumane)-2-(p-hydroxyphenyl)imidazolinide,
bis(tris(pentafluorophenyl)alumane)-2-(p-hydroxyphenyl)-1,3,4-triazolide,
bis(tris(pentafluorophenyl)alumane)-2-(p-hydroxyphenyl)-4,5-benziimidazolide;
bis(tris(pentafluorophenyl)alumane)-2-(p-trimethylsiloxyphenyl)imidazolide, bis(tris(pentafluorophenyl)alumane)-2-undecyl-4-(p-trimethylsiloxyphenyl)imidazolide,
bis(tris(pentafluorophenyl)alumane)-2-heptadecyl-4-(p-trimethylsiloxyphenyl)imidazolide,
bis(tris(pentafluorophenyl)alumane)-2-(p-trimethylsiloxyphenyl)-4,5-bis(undecyl)imidazolide,
bis(tris(pentafluorophenyl)alumane)-2-(p-trimethylsiloxyphenyl)-4,5-bis(heptadecyl)imidazolide,
bis(tris(pentafluorophenyl)alumane)-2-(p-trimethylsiloxyphenyl)imidazolinide,
bis(tris(pentafluorophenyl)alumane)-2-(p-trimethylsiloxyphenyl)-1,3,4-triazolide,
bis(tris(pentafluorophenyl)alumane)-2-(p-trimethylsiloxyphenyl)-4,5-benziimidazolide,
bis(tris(pentafluorophenyl)alumane)-2-(p-diethylaluminoxyphenyl)imidazolide,
bis(tris(pentafluorophenyl)alumane)-2-undecyl-4-(p-diethylaluminoxyphenyl)imidazolide,
bis(tris(pentafluorophenyl)alumane)-2-heptadecyl-4-(p-diethylaluminoxyphenyl)imidazolide,
bis(tris(pentafluorophenyl)alumane)-2-(p-diethylaluminoxyphenyl)-4,5-bis(undecyl)imidazolide,
bis(tris(pentafluorophenyl)alumane)-2-(p-diethylaluminoxyphenyl)-4,5-bis(heptadecyl)imidazolide,
bis(tris(pentafluorophenyl)alumane)-2-(p-diethylaluminoxyphenyl)imidazolinide,
bis(tris(pentafluorophenyl)alumane)-2-(p-diethylaluminoxyphenyl)-1,3,4-triazolide, and
bis(tris(pentafluorophenyl)alumane)-2-(p-diethylaluminoxyphenyl)-4,5-benziimidazolide.

The compounds may be prepared by a condensation reaction between the alkali metal salt of the anion, $Z^*$, and a Lewis acid, $J^*$, preferably under phase transfer conditions, using for example a crown ether to solubilize the alkali metal salt if necessary, followed by a metathesis reaction with the corresponding halide salt of the cation, $A^{*+a}$. Certain of the cocatalysts are also amenable to preparation via a one step, single reactor process. For example, the ammonium- or phosphonium-substituted hydroxyl group or quiescent reactive group-substituted imidiazolide salts can be prepared by contacting the Lewis acid, $J^*$, or its Lewis base adduct, such as an etherate, with the neutral compound corresponding to the anion, $Z^*$. Both reactants are desirably relatively lipophilic, such that the reaction can be performed in non-polar solvents. Addition of the free base corresponding to the cation, $A^{*+a}$, results in formation of the charge separated species, which may be recovered from the reaction mixture by devolatilization or used without further purification.

The corresponding reactive hydroxyl-, thiol, amine, or phosphine containing compound (or its metal or ammonium salt derivative) may be generated or produced in situ by reaction of the quiescent reactive groups of the present compounds with any suitable reactant, such as a hydrocarbon, a metal fluoride, an ammonium fluoride, or an acid, thereby removing the capping or protecting group(s).

Due to the presence of the hydroxyl group or quiescent reactive functionality in the compounds of the present invention, or reactive derivatives thereof, the present compounds may be readily attached to a reactive substrate, such as a particulated solid containing reactive hydrocarbyl groups, especially hydrocarbylmetal- or hydrocarbylmetalloid-functionality. Examples include alumina, silica, aluminosilicates, and aluminum magnesium silicate materials, containing reactive hydroxyl- or hydrocarbyl-functionality, and such materials treated with any substance to impart reactive metal-hydrocarbyl or metalloid-hydrocarbyl functionality. Examples of such treating substances include trihydrocarbyl aluminum compounds, chlorosilane compounds, and mono- or di-hydrocarbylsilane compounds that react with a portion or all of reactive surface hydroxyl functionality of the substrate to form a "capped" derivative. This technique is known in the art and disclosed for example in U.S. Pat. No. 6,087,293.

Suitable catalysts for use in combination with the foregoing cocatalysts include any compound or complex of a metal of Groups 3–10 of the Periodic Table of the Elements capable of being activated to polymerize ethylenically unsaturated compounds by the present activators. Examples include Group 10 diimine derivatives corresponding to the formula:

wherein
  $M^*$ is Ni(II) or Pd(II);
  K is halo, hydrocarbyl, or hydrocarbyloxy;
  and the two nitrogen atoms are linked by a bridging system.

Such catalysts have been previously disclosed in *J. Am. Chem. Soc.*, 118, 267–268 (1996), *J. Am. Chem. Soc.*, 117, 6414–6415 (1995), and *Organometallics*, 16, 1514–1516, (1997).

Additional catalysts include derivatives of Group 3, 4, or Lanthanide metals which are in the +2, +3, or +4 formal oxidation state. Preferred compounds include metal complexes containing from 1 to 3 π-bonded anionic or neutral ligand groups, which may be cyclic or non-cyclic delocalized π-bonded anionic ligand groups. Exemplary of such π-bonded anionic ligand groups are conjugated or nonconjugated, cyclic or non-cyclic dienyl groups, allyl groups, boratabenzene groups, phosphole, and arene groups. By the term "π-bonded" is meant that the ligand group is bonded to the transition metal by a sharing of electrons from a partially delocalized π-bond.

Each atom in the delocalized π-bonded group may independently be substituted with a radical selected from the group consisting of hydrogen, halogen, hydrocarbyl, halohydrocarbyl, hydrocarbyl-substituted metalloid radicals wherein the metalloid is selected from Group 14 of the Periodic Table of the Elements, and such hydrocarbyl- or hydrocarbyl-substituted metalloid radicals further substituted with a Group 15 or 16 hetero atom containing moiety. Included within the term "hydrocarbyl" are $C_{1-20}$ straight, branched and cyclic alkyl radicals, $C_{6-20}$ aromatic radicals, $C_{7-20}$ alkyl-substituted aromatic radicals, and $C_{7-20}$ aryl-substituted alkyl radicals. In addition two or more such radicals may together form a fused ring system, including partially or fully hydrogenated fused ring systems, or they may form a metallocycle with the metal. Suitable hydrocarbyl-substituted organometalloid radicals include mono-, di- and tri-substituted organometalloid radicals of Group 14 elements wherein each of the hydrocarbyl groups contains from 1 to 20 carbon atoms. Examples of suitable hydrocarbyl-substituted organometalloid radicals include trimethylsilyl, triethylsilyl, ethyldimethylsilyl, methyldiethylsilyl, triphenylgermyl, and trimethylgermyl groups. Examples of Group 15 or 16 hetero atom containing moieties include amine, phosphine, ether or thioether moieties or divalent derivatives thereof, e.g. amide, phosphide, ether or thioether groups bonded to the transition metal or Lanthanide metal, and bonded to the hydrocarbyl group or to the hydrocarbyl-substituted metalloid containing group.

Examples of suitable anionic, delocalized π-bonded groups include cyclopentadienyl, indenyl, fluorenyl, tetrahydroindenyl, tetrahydrofluorenyl, octahydrofluorenyl, pentadienyl, cyclohexadienyl, dihydroanthracenyl, hexahydroanthracenyl, decahydroanthracenyl groups, phosphole, and boratabenzene groups, as well as hydrocarbyl-silyl- (including mono-, di-, or tri(hydrocarbyl) silyl) substituted derivatives thereof. Preferred anionic, delocalized π-bonded groups are cyclopentadienyl, pentamethylcyclopentadienyl, tetramethylcyclopentadienyl, tetramethyl(trimethylsilyl)-cyclopentadienyl, indenyl, 2,3-dimethylindenyl, fluorenyl, 2-methylindenyl, 2-methyl-4-phenylindenyl, tetrahydrofluorenyl, octahydrofluorenyl, and tetrahydroindenyl.

The boratabenzenes are anionic ligands that are boron containing analogues to benzene. They are previously known in the art having been described by G. Herberich, et al., in *Organometallics*, 14,1, 471–480 (1995). Preferred boratabenzenes correspond to the formula:

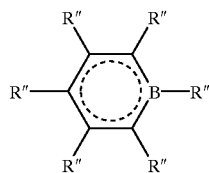

wherein R" is selected from the group consisting of hydrocarbyl, silyl, N,N-dihydrocarbylamino, or germyl, said R" having up to 20 non-hydrogen atoms. In complexes involving divalent derivatives of such delocalized π-bonded groups one atom thereof is bonded by means of a covalent bond or a covalently bonded divalent group to another atom of the complex thereby forming a bridged system.

Phospholes are anionic ligands that are phosphorus containing analogues to a cyclopentadienyl group. They are previously known in the art having been described by WO 98/50392, and elsewhere. Preferred phosphole ligands correspond to the formula:

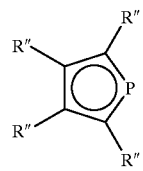

wherein R" is selected from the group consisting of hydrocarbyl, silyl, N,N-dihydrocarbylamino, or germyl, said R" having up to 20 non-hydrogen atoms, and optionally one or more R" groups may be bonded together forming a multicyclic fused ring system, or form a bridging group connected to the metal. In complexes involving divalent derivatives of such delocalized π-bonded groups one atom thereof is bonded by means of a covalent bond or a covalently bonded divalent group to another atom of the complex thereby forming a bridged system.

Phosphinimine/cyclopentadienyl complexes are disclosed in EP-A-890581 and correspond to the formula

wherein:

R* is a monovalent ligand, illustrated by hydrogen, halogen, or hydrocarbyl, or two R* groups together form a divalent ligand, M** is a Group 4 metal, Cp is cyclopentadienyl, or similar delocalized π-bonded group, $L^1$ is a monovalent ligand group, illustrated by hydrogen, halogen or hydrocarbyl, b is a number from 1 to 3; and n is 1 or 2.

A suitable class of catalysts are transition metal complexes corresponding to the formula:

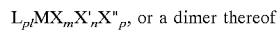

wherein:

Lp is an anionic, delocalized, π-bonded group that is bound to M, containing up to 50 non-hydrogen atoms, optionally two Lp groups may be joined together forming a bridged structure, and further optionally one Lp may be bound to X;

M is a metal of Group 4 of the Periodic Table of the Elements in the +2, +3 or +4 formal oxidation state;

X is an optional, divalent group of up to 50 non-hydrogen atoms that together with Lp forms a metallocycle with M;

X' is an optional neutral ligand having up to 20 non-hydrogen atoms;

X" each occurrence is a monovalent, anionic moiety having up to 40 non-hydrogen atoms, optionally, two X" groups may be covalently bound together forming a divalent dianionic moiety having both valences bound to M, or, optionally 2 X" groups may be covalently bound together to form a neutral, conjugated or nonconjugated diene that is π-bonded to M (whereupon M is in the +2 oxidation state), or further optionally one or more X" and one or more X' groups may be bonded together thereby forming a moiety that is both covalently bound to M and coordinated thereto by means of Lewis base functionality;

l is 0, 1 or 2;

m is 0 or 1;

n is a number from 0 to 3;

p is an integer from 0 to 3; and the sum, l+m+p, is equal to the formal oxidation state of M, except when 2 X" groups together form a neutral conjugated or non-conjugated diene that is π-bonded to M, in which case the sum l+m is equal to the formal oxidation state of M.

Preferred complexes include those containing either one or two Lp groups. The latter complexes include those containing a bridging group linking the two Lp groups. Preferred bridging groups are those corresponding to the formula $(ER^*_2)_x$, $B(NR^{}_2)$, or $B(NR^{}_2)_2$, wherein E is silicon, germanium, tin, or carbon, R* independently each occurrence is hydrogen or a group selected from silyl, hydrocarbyl, hydrocarbyloxy, and combinations thereof, said R* having up to 30 carbon or silicon atoms, R independently each occurrence is a group selected from silyl, hydrocarbyl, and combinations thereof, said R having up to 30 carbon or silicon atoms, and x is 1 to 8. Preferably, R* independently each occurrence is methyl, ethyl, propyl, benzyl, butyl, phenyl, methoxy, ethoxy, or phenoxy, and R** is methyl, ethyl, propyl, benzyl or butyl.

Examples of the complexes containing two Lp groups are compounds corresponding to the formula:

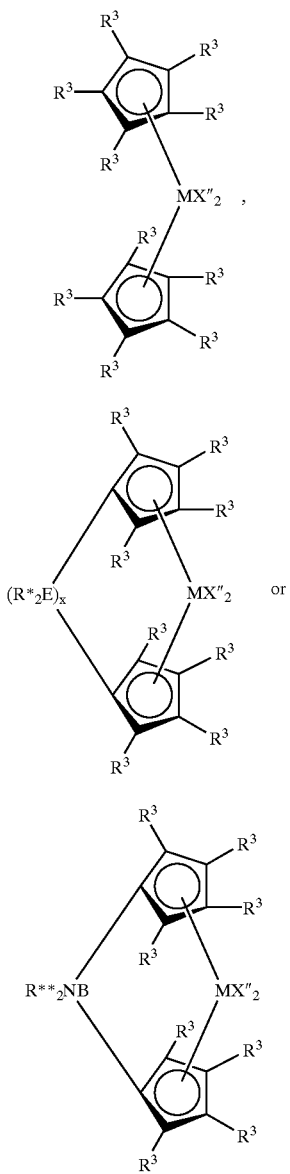

wherein:
M is titanium, zirconium or hafnium, preferably zirconium or hafnium, in the +2 or +4 formal oxidation state;
$R^3$ in each occurrence independently is selected from the group consisting of hydrogen, hydrocarbyl, silyl, germyl, cyano, halo and combinations thereof, said $R^3$ having up to 20 non-hydrogen atoms, or adjacent $R^3$ groups together form a divalent derivative (that is, a hydrocarbadiyl, siladiyl or germadiyl group) thereby forming a fused ring system, and
X" independently each occurrence is an anionic ligand group of up to 40 non-hydrogen atoms, or two X" groups together form a divalent anionic ligand group of up to 40 non-hydrogen atoms or together are a conjugated diene having from 4 to 30 non-hydrogen atoms forming a π-complex with M, whereupon M is in the +2 formal oxidation state, and
$R^*$, $R^{**}$, E and x are as previously defined, preferably $(ER^*_2)_x$ is dimethylsilandiyl or ethylene, and $BNR^{**}_2$ is di(isopropyl)aminoborandiyl.

The foregoing metal complexes are especially suited for the preparation of polymers having stereoregular molecular structure. In such capacity it is preferred that the complex possesses $C_s$ symmetry or possesses a chiral, stereorigid structure. Examples of the first type are compounds possessing different delocalized π-bonded systems, such as one cyclopentadienyl group and one fluorenyl group. Similar systems based on Ti(IV) or Zr(IV) were disclosed for preparation of syndiotactic olefin polymers in Ewen, et al., J. Am. Chem. Soc. 110, 6255–6256 (1980). Examples of chiral structures include rac bis-indenyl complexes. Similar systems based on Ti(IV) or Zr(IV) were disclosed for preparation of isotactic olefin polymers in Wild et al., J. Organomet. Chem., 232, 233–47, (1982).

Exemplary bridged ligands containing two π-bonded groups are: dimethylbis(cyclopentadienyl)silane, dimethylbis(tetramethylcyclopentadienyl)silane, dimethylbis(2-ethylcyclopentadien-1-yl)silane, dimethylbis(2-t-butylcyclopentadien-1-yl)silane, 2,2-bis(tetramethylcyclopentadienyl)propane, dimethylbis(inden-1-yl)silane, dimethylbis(tetrahydroinden-1-yl)silane, dimethylbis(fluoren-1-yl)silane, dimethylbis(tetrahydrofluoren-1-yl)silane, dimethylbis(2-methyl-4-phenylinden-1-yl)silane, dimethylbis(2-methylinden-1-yl) silane, di(isopropyl)aminobis(cyclopentadien-1-yl)borandiyl, di(isopropyl)aminobis(2-methyl-4-phenylinden-1-yl)-borandiyl, di(isopropyl)aminobis(2-methylinden-1-yl)borandiyl, dimethyl(cyclopentadienyl)(fluoren-1-yl)silane, dimethyl(cyclopentadienyl)(octahydrofluoren-1-yl)silane, dimethyl(cyclopentadienyl)(tetrahydrofluoren-1-yl)silane, (1,1,2,2-tetramethy)-1,2-bis(cyclopentadienyl)disilane, (1,2-bis(cyclopentadienyl)ethane, and dimethyl(cyclopentadienyl)-1-(fluoren-1-yl)methane.

Preferred X" groups are selected from hydride, hydrocarbyl, silyl, germyl, halohydrocarbyl, halosilyl, silylhydrocarbyl and aminohydrocarbyl groups, or two X" groups together form a divalent derivative of a conjugated diene or else together they form a neutral, π-bonded, conjugated diene. Most preferred X" groups are $C_{1-20}$ hydrocarbyl groups.

Complexes containing two Lp groups including bridged complexes suitable for use in the present invention include:
bis(cyclopentadienyl)zirconiumdimethyl,
bis(cyclopentadienyl)zirconium dibenzyl,
bis(cyclopentadienyl)zirconium methyl benzyl,
bis(cyclopentadienyl)zirconium methyl phenyl,
bis(cyclopentadienyl)zirconiumdiphenyl,
bis(cyclopentadienyl)titanium-allyl,
bis(cyclopentadienyl)zirconiummethylmethoxide,
bis(cyclopentadienyl)zirconiummethylchloride,
bis(pentamethylcyclopentadienyl)zirconiumdimethyl,
bis(pentamethylcyclopentadienyl)titaniumdimethyl,
bis(indenyl)zirconiumdimethyl,
indenylfluorenylzirconiumdimethyl,
bis(indenyl)zirconiummethyl(2-(dimethylamino)benzyl),
bis(indenyl)zirconiummethyltrimethylsilyl,
bis(tetrahydroindenyl)zirconiummethyltrimethylsilyl,
bis(pentamethylcyclopentadienyl)zirconiummethylbenzyl,
bis(pentamethylcyclopentadienyl)zirconiumdibenzyl,
bis(pentamethylcyclopentadienyl) zirconiummethylmethoxide,
bis(pentamethylcyclopentadienyl)zirconiummethylchloride,
bis(methylethylcyclopentadienyl)zirconiumdimethyl,
bis(butylcyclopentadienyl)zirconiumdibenzyl,
bis(t-butylcyclopentadienyl)zirconiumdimethyl,
bis(ethyltetramethylcyclopentadienyl)zirconiumdimethyl,
bis(methylpropylcyclopentadienyl)zirconiumdibenzyl, bis(trimethylsilylcyclopentadienyl)zirconiumdibenzyl,
dimethylsilyl-bis(cyclopentadienyl)zirconiumdimethyl,
dimethylsilyl-bis(tetramethylcyclopentadienyl)titanium (III) allyl
dimethylsilyl-bis(t-butylcyclopentadienyl) zirconiumdibenzyl,
dimethylsilyl-bis(n-butylcyclopentadienyl)zirconium bis(trimethylsilyl),
(methylene-bis(tetramethylcyclopentadienyl)titanium(III) 2-(dimethylamino)benzyl,
(methylene-bis(n-butylcyclopentadienyl)titanium(III) 2-(dimethylamino)benzyl,
dimethylsilyl-bis(indenyl)zirconiumbenzylchloride,
dimethylsilyl-bis(2-methylindenyl)zirconiumdimethyl,
dimethylsilyl-bis(2-methyl-4-phenylindenyl) zirconiumdimethyl,
dimethylsilyl-bis(2-methylindenyl)zirconium-1,4-diphenyl-1,3-butadiene,
dimethylsilyl-bis(2-methyl-4-phenylindenyl)zirconium (II) 1,4-diphenyl-1,3-butadiene, dimethylsilyl-bis(tetrahydroindenyl)zirconium (II) 1,4-diphenyl-1,3-butadiene,
di(isopropylamino)borandiylbis(2-methyl-4-phenylindenyl) zirconium dimethyl,
dimethylsilyl-bis(tetrahydrofluorenyl)zirconium bis(trimethylsilyl),
(isopropylidene)(cyclopentadienyl)(fluorenyl) zirconiumdibenzyl, and
dimethylsilyl(tetramethylcyclopentadienyl)(fluorenyl) zirconium dimethyl.

A further class of metal complexes utilized in the present invention corresponds to the preceding formula

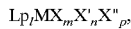

or a dimer thereof, wherein X is a divalent group of up to 50 non-hydrogen atoms that together with Lp forms a metallocycle with M.

Preferred divalent X groups include groups containing up to 30 non-hydrogen atoms comprising at least one atom that is oxygen, sulfur, boron or a member of Group 14 of the Periodic Table of the Elements directly attached to the delocalized =-bonded group, and a different atom, selected from the group consisting of nitrogen, phosphorus, oxygen or sulfur that is covalently bonded to M.

A preferred class of such Group 4 metal coordination complexes used according to the present invention corresponds to the formula:

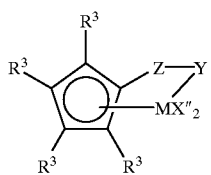

wherein:
M is titanium or zirconium, preferably titanium in the +2, +3, or +4 formal oxidation state;
$R^3$ in each occurrence independently is selected from the group consisting of hydrogen, hydrocarbyl, silyl, germyl, cyano, halo and combinations thereof, said $R^3$ having up to 20 non-hydrogen atoms, or adjacent $R^3$ groups together form a divalent derivative (that is, a hydrocarbadiyl, siladiyl or germadiyl group) thereby forming a fused ring system, each X" is a halo, hydrocarbyl, hydrocarbyloxy or silyl group, said group having up to 20 non-hydrogen atoms, or two X" groups together form a neutral $C_{5-30}$ conjugated diene or a divalent derivative thereof;
Y is —O—, —S—, —NR*—, —PR*—; and
Z is $SiR^*_2$, $CR^*_2$, $SiR^*_2SiR^*_2$, $CR^*_2CR^*_2$, $CR^*=CR^*$, $CR^*_2SiR^*_2$, $GeR^*_2$, or $B(NR^{**}_2)$ wherein R* and R** are as previously defined.

Illustrative Group 4 metal complexes of the latter formula that may be employed in the practice of the present invention include:
cyclopentadienyltitaniumtrimethyl,
indenyltitaniumtrimethyl,
octahydrofluorenyltitaniumtrimethyl,
tetrahydroindenyltitaniumtrimethyl,
tetrahydrofluorenyltitaniumtrimethyl,
(tert-butylamido)(1,1-dimethyl-2,3,4,9,10-η-1,4,5,6,7,8-hexahydronaphthalenyl)dimethylsilanetitaniumdimethyl,
(tert-butylamido)(1,1,2,3-tetramethyl-2,3,4,9,10-η-1,4,5,6,7,8-hexahydronaphthalenyl) dimethylsilanetitaniumdimethyl,
(tert-butylamido)(tetramethyl-$η^5$-cyclopentadienyl) dimethylsilanetitanium dibenzyl,
(tert-butylamido)(tetramethyl-$η^5$-cyclopentadienyl) dimethylsilanetitanium dimethyl,
(tert-butylamido)(tetramethyl-$η^5$-cyclopentadienyl)-1,2-ethanediyltitanium dimethyl,
(tert-butylamido)(tetramethyl-$η^5$-indenyl) dimethylsilanetitanium dimethyl,
(tert-butylamido)(tetramethyl-$η^5$-cyclopentadienyl) dimethylsilane titanium (III) 2-(dimethylamino)benzyl;
(tert-butylamido)(tetramethyl-$η^5$-cyclopentadienyl) dimethylsilanetitanium (III) allyl,
(tert-butylamido)(tetramethyl-$η^5$-cyclopentadienyl) dimethylsilanetitanium (III) 2,4-dimethylpentadienyl,
(tert-butylamido)(tetramethyl-$η^5$-cyclopentadienyl) dimethylsilanetitanium (II) 1,4-diphenyl-1,3-butadiene,
(tert-butylamido)(tetramethyl-$η^5$-cylopentadienyl) dimethylsilanetitanium (II) 1,3-pentadiene,
(tert-butylamido)(2-methylindenyl)dimethylsilanetitanium (ii) 1,4-diphenyl-1,3-butadiene,
(tert-butylamido)(2-methylindenyl)dimethylsilanetitanium (II) 2,4-hexadiene,
(tert-butylamido)(2-methylindenyl)dimethylsilanetitanium (IV) 2,3-dimethyl-1,3-butadiene,
(tert-butylamido)(2-methylindenyl)dimethylsilanetitanium (IV) isoprene,
(tert-butylamido)(2-methylindenyl)dimethylsilanetitanium (IV) 1,3-butadiene,
(tert-butylamido)(2,3-dimethylindenyl) dimethylsilanetitanium (IV) 2,3-dimethyl-1,3-butadiene,
(tert-butylamido)(2,3-dimethylindenyl) dimethylsilanetitanium (IV) isoprene
(tert-butylamido)(2,3-dimethylindenyl) dimethylsilanetitanium (IV) dimethyl
(tert-butylamido)(2,3-dimethylindenyl) dimethylsilanetitanium (IV) dibenzyl
(tert-butylamido)(2,3-dimethylindenyl) dimethylsilanetitanium (IV) 1,3-butadiene,
(tert-butylamido)(2,3-dimethylindenyl) dimethylsilanetitanium (II), 1,3-pentadiene,
(tert-butylamido)(2,3-dimethylindenyl) dimethylsilanetitanium (II) 1,4-diphenyl-1,3-butadiene,
(tert-butylamido)(2-methylindenyl)dimethylsilanetitanium (II) 1,3-pentadiene,
(tert-butylamido)(2-methylindenyl)dimethylsilanetitanium (IV) dimethyl, (tert-butylamido)(2-methylindenyl)dimethylsilanetitanium (IV) dibenzyl,
(tert-butylamido)(2-methyl-4-phenylindenyl) dimethylsilanetitanium (II), 1,4-diphenyl-1,3-butadiene,
(tert-butylamido)(2-methyl-4-phenylindenyl) dimethylsilanetitanium (II) 1,3-pentadiene,
(tert-butylamido)(2-methyl-4-phenylindenyl) dimethylsilanetitanium (II) 2,4-hexadiene,
(tert-butylamido)(tetramethyl-$\eta^5$-cyclopentadienyl) dimethyl-silanetitanium (IV) 1,3-butadiene,
(tert-butylamido)(tetramethyl-$\eta^5$-cyclopentadienyl) dimethylsilanetitanium (IV) 2,3-dimethyl-1,3-butadiene,
(tert-butylamido)(tetramethyl-$\eta^5$-cyclopentadienyl) dimethylsilanetitanium (IV) isoprene,
(tert-butylamido)(tetramethyl-$\eta^5$-cyclopentadienyl) dimethyl-silanetitanium (II) 1,4-dibenzyl-1,3-butadiene,
(tert-butylamido)(tetramethyl-$\eta^5$-cyclopentadienyl) dimethylsilanetitanium (II) 2,4-hexadiene,
(tert-butylamido)(tetramethyl-$\eta^5$-cyclopentadienyl) dimethyl-silanetitanium (II) 3-methyl-1,3-pentadiene,
(tert-butylamido)(2,4-dimethylpentadien-3-yl) dimethylsilanetitaniumdimethyl, (tert-butylamido)(6,6-dimethylcyclohexadienyl) dimethylsilanetitaniumdimethyl,
(tert-butylamido)(1,1-dimethyl-2,3,4,9,10-$\eta$-1,4,5,6,7,8-hexahydronaphthalen-4-yl) dimethylsilanetitaniumdimethyl,
(tert-butylamido)(1,1,2,3-tetramethyl-2,3,4,9,10-$\eta$-1,4,5,6,7,8-hexahydronaphthalen-4-yl) dimethylsilanetitaniumdimethyl
(tert-butylamido)(tetramethyl-$\eta^5$-cyclopentadienyl methylphenylsilanetitanium (IV) dimethyl,
(tert-butylamido)(tetramethyl-$\eta^5$-cyclopentadienyl methylphenylsilanetitanium (II) 1,4-diphenyl-1,3-butadiene,
1-(tert-butylamido)-2-(tetramethyl-$\eta^5$-cyclopentadienyl) ethanediyltitanium (IV) dimethyl,
1-(tert-butylamido)-2-(tetramethyl-$\eta^5$-cyclopentadienyl) ethanediyl titanium (II) 1,4-diphenyl-1,3-butadiene,
(tert-butylamido)(3-(N-pyrrolyl)indenyl) dimethylsilanetitanium (IV) 2,3-dimethyl-1,3-butadiene,
(tert-butylamido)(3-(N-pyrrolyl)indenyl) dimethylsilanetitanium (IV) isoprene
(tert-butylamido)(3-(N-pyrrolyl)indenyl) dimethylsilanetitanium (IV) dimethyl
(tert-butylamido)(3-(N-pyrrolyl)indenyl) dimethylsilanetitanium (IV) dibenzyl
(tert-butylamido)(3-(N-pyrrolyl)indenyl) dimethylsilanetitanium (IV) 1,3-butadiene,
(tert-butylamido)(3-(N-pyrrolyl)indenyl) dimethylsilanetitanium (II) 1,3-pentadiene,
(tert-butylamido)(3-(N-pyrrolyl)indenyl) dimethylsilanetitanium (II) 1,4-diphenyl-1,3-butadiene, and
(tert-butylamido)(3-N-pyrrolidinylinden-1-yl) dimethylsilanetitanium (IV) dimethyl.

Other catalysts, especially catalysts containing other Group 4 metals, will, of course, be apparent to those skilled in the art. Most highly preferred metal complexes for use herein are the following metal complexes:
(t-butylamido)dimethyl(tetramethylcyclopentadienyl) silanetitanium dimethyl,
(t-butylamido)dimethyl(tetramethylcyclopentadienyl) silanetitanium (II) 1,3-pentadiene,
(t-butylamido)dimethyl(tetramethylcyclopentadienyl) silanetitanium (II) 1,4 diphenyl-1,3-butadiene,
(cyclohexylamido)dimethyl(tetramethylcyclopentadienyl) silanetitanium dimethyl, cyclohexylamido)dimethyl (tetramethylcyclopentadienyl)silanetitanium (II) 1,3-pentadiene, cyclohexylamido)dimethyl (tetramethylcyclopentadienyl)silanetitanium (II) 1,4 diphenyl-1,3-butadiene,
(cyclododecylamido)dimethyl (tetramethylcyclopentadienyl)silanetitanium dimethyl,
(cyclododecylamido)dimethyl (tetramethylcyclopentadienyl)silanetitanium (II) 1,3-pentadiene,
(cyclododecylamido)dimethyl (tetramethylcyclopentadienyl)silanetitanium (II) 1,4 diphenyl-1,3-butadiene,
(t-butylamido)dimethyl(2-methyl-s-indacen-1-yl) silanetitanium dimethyl,
(t-butylamido)dimethyl(2-methyl-s-indacen-1-yl) silanetitanium (II) 1,3-pentadiene,
(t-butylamido)dimethyl(2-methyl-s-indacen-1-yl) silanetitanium (II) 1,4 diphenyl-1,3-butadiene,
(cyclohexylamido)dimethyl(2-methyl-s-indacen-1-yl) silanetitanium dimethyl, cyclohexylamido)dimethyl(2-methyl-s-indacen-1-yl)silanetitanium (II) 1,3-pentadiene, cyclohexylamido)dimethyl(2-methyl-s-indacen-1-yl) silanetitanium(II) 1,4 diphenyl-1,3-butadiene,
(cyclododecylamido)dimethyl(2-methyl-s-indacen-1-yl) silanetitanium dimethyl,
(cyclododecylamido)dimethyl(2-methyl-s-indacen-1-yl) silanetitanium(II) 1,3-pentadiene,
(cyclododecylamido)dimethyl(2-methyl-s-indacen-1-yl) silanetitanium(II) 1,4diphenyl-1,3-butadiene,
(t-butylamido)dimethyl(3,4-(cyclopenta(I)phenanthren-1-yl)silanetitanium dimethyl,
(t-butylamido)dimethyl(3,4-(cyclopenta(I)phenanthren-1-yl)silanetitanium(II) 1,3-pentadiene,
(t-butylamido)dimethyl(3,4-(cyclopenta(I)phenanthren-1-yl)silanetitanium(II) 1,4 diphenyl-1,3-butadiene,
(cyclohexylamido)dimethyl(3,4-(cyclopenta(I)phenanthren-1-yl)silanetitanium dimethyl, cyclohexylamido)dimethyl (3,4-(cyclopenta(I)phenanthren-1-yl)silanetitanium(II) 1,3-pentadiene, cyclohexylamido)dimethyl(3,4-(cyclopenta(I)phenanthren-1-yl)silanetitanium(II) 1,4 diphenyl-1,3-butadiene,
(cyclododecylamido)dimethyl(3,4-(cyclopenta(I) phenanthren-1-yl)silanetitanium dimethyl,
(cyclododecylamido)dimethyl(3,4-(cyclopenta(I) phenanthren-1-yl)silanetitanium(II) 1,3-pentadiene,
(cyclododecylamido)dimethyl(3,4-(cyclopenta(I) phenanthren-1-yl)silanetitanium(II) 1,4 diphenyl-1,3-butadiene,
(t-butylamido)dimethyl(2-methyl-4-phenylinden-1-yl) silanetitanium dimethyl,
(t-butylamido)dimethyl(2-methyl-4-phenylinden-1-yl) silanetitanium(II) 1,3-pentadiene,
(t-butylamido)dimethyl(2-methyl-4-phenylinden-1-yl) silanetitanium(II) 1,4 diphenyl-1,3-butadiene,
(cyclohexylamido)dimethyl(2-methyl-4-phenylinden-1-yl) silanetitanium dimethyl, cyclohexylamido)dimethyl(2-methyl-4-phenylinden-1-yl)silanetitanium(II) 1,3-pentadiene, cyclohexylamido)dimethyl(2-methyl-4-phenylinden-1-yl)silanetitanium(II)1,4 diphenyl-1,3-butadiene,
(cyclododecylamido)dimethyl(2-methyl-4-phenylinden-1-yl)silanetitanium dimethyl,
(cyclododecylamido)dimethyl(2-methyl-4-phenylinden-1-yl)silanetitanium(II) 1,3-pentadiene,
(cyclododecylamido)dimethyl(2-methyl-4-phenylinden-1-yl)silanetitanium(II) 1,4 diphenyl-1,3-butadiene,
(t-butylamido)dimethyl(2-methyl-4-phenylinden-1-yl) silanetitanium dimethyl, (t-butylamido)dimethyl(2-methyl-4-phenylinden-1-yl)
  silanetitanium (II) 1,3-pentadiene,
(t-butylamido)dimethyl(2-methyl-4-phenylinden-1-yl)
  silanetitanium (II) 1,4 diphenyl-1,3-butadiene,
(cyclohexylamido)dimethyl(2-methyl-4-phenylinden-1-yl)
  silanetitanium dimethyl, cyclohexylamido)dimethyl(2-
  methyl-4-phenylinden-1-yl)silanetitanium((II) 1,3-
  pentadiene, cyclohexylamido)dimethyl(2-methyl-4-
  phenylinden-1-yl)silanetitanium(II) 1,4 diphenyl-1,3-
  butadiene,
(cyclododecylamido)dimethyl(2-methyl-4-phenylinden-1-
  yl)silanetitanium dimethyl,
(cyclododecylamido)dimethyl(2-methyl-4-phenylinden-1-
  yl)silanetitanium(II) 1,3-pentadiene,
(cyclododecylamido)dimethyl(2-methyl-4-phenylinden-1-
  yl)silanetitanium(II) 1,4 diphenyl-1,3-butadiene,
(t-butylamido)dimethyl(3-(1-pyrrolidinyl)inden-1-yl)
  silanetitanium dimethyl,
(t-butylamido)dimethyl(3-(1-pyrrolidinyl)inden-1-yl)
  silanetitanium(II) 1,3-pentadiene,
(t-butylamido)dimethyl(3-(1-pyrrolidinyl)inden-1-yl)
  silanetitanium(II) 1,4 diphenyl-1,3-butadiene,
(cyclohexylamido)dimethyl(3-(1-pyrrolidinyl)inden-1-yl)
  silanetitanium dimethyl, cyclohexylamido)dimethyl(3-(1-
  pyrrolidinyl)inden-1-yl)silanetitanium(II) 1,3-pentadiene,
  cyclohexylamido)dimethyl(3-(1-pyrrolidinyl)inden-1-yl)
  silanetitanium(II) 1,4 diphenyl-1,3-butadiene,
(cyclododecylamido)dimethyl(3-(1-pyrrolidinyl)inden-1-yl)
  silanetitanium dimethyl,
(cyclododecylamido)dimethyl(3-(1-pyrrolidinyl)inden-1-yl)
  silanetitanium(II) 1,3-pentadiene,
(cyclododecylamido)dimethyl(3-(1-pyrrolidinyl)inden-1-yl)
  silanetitanium(II) 1,4 diphenyl-1,3-butadiene,
(t-butylamido)dimethyl(3-(1-pyrrolidinyl)inden-1-yl)
  silanetitanium dimethyl,
(t-butylamido)dimethyl(3-(1-pyrrolidinyl)inden-1-yl)
  silanetitanium (II)1,3-pentadiene,
(t-butylamido)dimethyl(3-(1-pyrrolidinyl)inden-1-yl)
  silanetitanium (II) 1,4 diphenyl-1,3-butadiene,
(cyclohexylamido)dimethyl(3-(1-pyrrolidinyl)inden-1-yl)
  silanetitanium dimethyl, cyclohexylamido)dimethyl(3-(1-
  pyrrolidinyl)inden-1-yl)silanetitanium(II) 1,3-pentadiene,
  cyclohexylamido)dimethyl(3-(1-pyrrolidinyl)inden-1-yl)
  silanetitanium(II) 1,4 diphenyl-1,3-butadiene,
(cyclododecylamido)dimethyl(3-(1-pyrrolidinyl)inden-1-yl)
  silanetitanium dimethyl,
(cyclododecylamido)dimethyl(3-(1-pyrrolidinyl)inden-1-yl)
  silanetitanium(II) 1,3-pentadiene,
(cyclododecylamido)dimethyl(3-(1-pyrrolidinyl)inden-1-yl)
  silanetitanium(II) 1,4 diphenyl-1,3-butadiene,
1,2-ethanebis(inden-1-yl)zirconium dimethyl,
1,2-ethanebis(inden-1-yl)zirconium(II) 1,3-pentadiene, 1,2-
  ethanebis(inden-1-yl)zirconium(II) 1,4 diphenyl-1,3-
  butadiene,
1,2-ethanebis(2-methyl-4-phenylinden-1-yl)zirconium
  dimethyl,
1,2-ethanebis(2-methyl-4-phenylinden-1-yl)zirconium(II)
  1,3-pentadiene,
1,2-ethanebis(2-methyl-4-phenylinden-1-yl)zirconium(II)
  1,4 diphenyl-1,3-butadiene,
dimethylsilanebis(inden-1-yl)zirconium dimethyl,
dimethylsilanebis(inden-1-yl)zirconium(II) 1,3-pentadiene,
dimethylsilanebis(inden-1-yl)zirconium(II) 1,4 diphenyl-1,
  3-butadiene,
dimethylsilanebis(2-methyl-4-phenylinden-1-yl)zirconium
  dimethyl,
dimethylsilanebis(2-methyl-4-phenylinden-1-yl)zirconium
  (II) 1,3-pentadiene, and
dimethylsilanebis(2-methyl-4-phenylinden-1-yl)zirconium
  (II) 1,4 diphenyl-1,3-butadiene.

The expanded anion cocatalysts of the invention may also be used in combination with an oligomeric or polymeric alumoxane compound, a tri(hydrocarbyl)aluminum compound, a di(hydrocarbyl) (hydrocarbyloxy)aluminum compound, a di(hydrocarbyl)(dihydrocarbyl-amido) aluminum compound, a bis(dihydrocarbyl-amido) (hydrocarbyl)aluminum compound, a di(hydrocarbyl)amido (disilyl)aluminum compound, a di(hydrocarbyl)amido (hydrocarbyl)(silyl)aluminum compound, a bis (dihydrocarbylamido)(silyl)aluminum compound, or a mixture of the foregoing compounds, having from 1 to 20 non-hydrogen atoms in each hydrocarbyl, hydrocarbyloxy, or silyl group, if desired. These aluminum compounds are usefully employed for their beneficial ability to scavenge impurities such as oxygen, water, and aldehydes from the polymerization mixture as well as to react with the hydroxyl group or quiescent reactive functionality of the compounds or the reactive derivatives thereof.

Preferred aluminum compounds include $C_{1-20}$ trialkyl aluminum compounds, especially those wherein the alkyl groups are ethyl, propyl, isopropyl, n-butyl, isobutyl, pentyl, neopentyl, or isopentyl, dialkyl(aryloxy)aluminum compounds containing from 1–6 carbons in the alkyl group and from 6 to 18 carbons in the aryl group (especially (3,5-di (t-butyl)-4-methylphenoxy)diisobutylaluminum), methylalumoxane, modified methalumoxane, especially isobutyl modified alumoxane, and tri(ethylaluminum)-, tris (pentafluorophenyl)borane-, or tris(pentafluorophenyl) aluminum-modified alumoxanes or supported derivatives thereof. (The latter compositions are previously known, having been disclosed in WO99/15534. Additional species include mixtures of aluminum containing Lewis acids as disclosed in pending U.S. patent applications Ser. Nos. 09/330,673 and 09/330,675. The molar ratio of activator to aluminum compound is preferably from 1:10,000 to 1000:1, more preferably from 1:5000 to 100:1, most preferably from 1:100 to 100:1.

The cocatalysts of the present invention are capable of activating a wide variety of metal complexes. Moreover, the cocatalysts can be optimized in their ability to activate different metal complexes through combination of anions, Z*, having Lewis base sites of varying base strength, and Lewis acids, J*, having varying acidity. Thus, use of derivatives of weakly basic anions such as dicyanamide, 1,2,4-triazolide and 4,5-dichloroimidazolide give expanded anion salts which are less active cocatalysts, all other variables being the same, than do derivatives of moderately basic anions, such as cyanide, azide, benzotriazolide, benzimidazolide and tetraimidazoylborate, which in turn give less active cocatalalysts than derivatives of even more basic anions, such as 4,4-dimethylimidazolinide, imidazolide, 5,6-dimethylbenzimidazolide and 2-undecylimidazolide.

The equivalent ratio of catalyst/cocatalyst (calculated based on quantity of metal in the catalyst and anionic charges on the cocatalyst) employed preferably ranges from 1:10 to 10:1, more preferably from 1:5 to 2:1, most preferably from 1:4 to 1:1. Mixtures of the activating cocatalysts of the present invention may also be employed if desired.

Suitable addition polymerizable monomers include ethylenically unsaturated monomers, acetylenic compounds, conjugated or non-conjugated dienes, and polyenes. Preferred monomers include olefins, for examples alpha-olefins having from 2 to 20,000, preferably from 2 to 20, more preferably from 2 to 8 carbon atoms and combinations of two or more of such alpha-olefins. Particularly suitable alpha-olefins include, for example, ethylene, propylene, 1-butene, 1-pentene, 4-methylpentene-1,1-hexene, 1-heptene, 1-octene, 1-nonene, 1-decene, 1-undecene, 1-dodecene, 1-tridecene, 1-tetradecene, 1-pentadecene, or combinations thereof, as well as long chain vinyl terminated oligomeric or polymeric reaction products formed during the polymerization, and $C_{10-30}$ α-olefins specifically added to the reaction mixture in order to produce relatively long chain branches in the resulting polymers. Preferably, the alpha-olefins are ethylene, propene, 1-butene, 4-methyl-pentene-1,1-hexene, 1-octene, and combinations of ethylene and/or propene with one or more of such other alpha-olefins. Other preferred monomers include styrene, halo- or alkyl substituted styrenes, vinylbenzocyclobutene, 1,4-hexadiene, dicyclopentadiene, ethylidene norbornene, and 1,7-octadiene. Mixtures of the above-mentioned monomers may also be employed.

In general, the polymerization may be accomplished at conditions well known in the prior art for Ziegler-Natta or Kaminsky-Sinn type polymerization reactions. Suspension, solution, slurry, gas phase or high pressure, whether employed in batch or continuous form or other process conditions, may be employed if desired. Examples of such well known polymerization processes are depicted in WO 88/02009, U.S. Pat. Nos. 5,084,534, 5,405,922, 4,588,790, 5,032,652, 4,543,399, 4,564,647, 4,522,987, and elsewhere. Preferred polymerization temperatures are from 0–250° C. Preferred polymerization pressures are from atmospheric to 3000 atmospheres.

Suitable processing conditions include solution polymerization, more preferably continuous solution polymerization processes, conducted in the presence of an aliphatic or alicyclic liquid diluent, preferably using the unsupported, quiescent reactive functionality containing compounds. By the term "continuous polymerization" is meant that at least the products of the polymerization are continuously removed from the reaction mixture, such as for example by devolatilization of a portion of the reaction mixture. Preferably one or more reactants are also continuously added to the polymerization mixture during the polymerization. Examples of suitable aliphatic or alicyclic liquid diluents include straight and branched-chain $C_{4-12}$ hydrocarbons and mixtures thereof; alicyclic hydrocarbons such as cyclohexane, cycloheptane, methylcyclohexane, methylcycloheptane, and mixtures thereof; and perfluorinated hydrocarbons such as perfluorinated $C_{4-10}$ alkanes, and the like. Suitable diluents also include aromatic hydrocarbons (particularly for use with aromatic α-olefins such as styrene or ring alkyl-substituted styrenes) including toluene, ethylbenzene or xylene, as well as liquid olefins (which may act as monomers or comonomers) including ethylene, propylene, butadiene, cyclopentene, 1-hexene, 3-methyl-1pentene, 4-methyl-1-pentene, 1,4-hexadiene, 1-octene, 1-decene, styrene, divinylbenzene, allylbenzene, vinyltoluene (including all isomers alone or in admixture), and the like. Mixtures of the foregoing are also suitable. The foregoing diluents may also be advantageously employed during the synthesis of the metal complexes and catalyst activators of the present invention.

In most polymerization reactions the molar ratio of catalyst:polymerizable compounds employed is from $10^{-12}$:1 to 0.1:1, more preferably from $10^{-12}$:1 to $10^{-5}$:1.

The catalyst composition of the invention may also be utilized in combination with at least one additional homogeneous or heterogeneous polymerization catalyst in separate reactors connected in series or in parallel to prepare polymer blends having desirable properties. An example of such a process is disclosed in WO 94/00500.

Molecular weight control agents can be used in combination with the present cocatalysts. Examples of such molecular weight control agents include hydrogen, trialkyl aluminum compounds or other known chain transfer agents. A particular benefit of the use of the present cocatalysts is the ability (depending on reaction conditions) to produce narrow molecular weight distribution α-olefin homopolymers and copolymers in greatly improved catalyst efficiencies. Preferred polymers have Mw/Mn of less than 2.5, more preferably less than 2.3. Such narrow molecular weight distribution polymer products are highly desirable due to improved tensile strength properties.

The catalyst composition of the present invention can also be employed to advantage in the gas phase polymerization and copolymerization of olefins. Gas phase processes for the polymerization of olefins, especially the homopolymerization and copolymerization of ethylene and propylene, and the copolymerization of ethylene with higher alpha olefins such as, for example, 1-butene, 1-hexene, 4-methyl-1-pentene are well known in the art. Such processes are used commercially on a large scale for the manufacture of high density polyethylene (HDPE), medium density polyethylene (MDPE), linear low density polyethylene (LLDPE) and polypropylene.

The gas phase process employed can be, for example, of the type which employs a mechanically stirred bed or a gas fluidized bed as the polymerization reaction zone. Preferred is the process wherein the polymerization reaction is carried out in a vertical cylindrical polymerization reactor containing a fluidized bed of polymer particles supported above a perforated plate, the fluidisation grid, by a flow of fluidisation gas.

The gas employed to fluidize the bed comprises the monomer or monomers to be polymerized, and also serves as a heat exchange medium to remove the heat of reaction from the bed. The hot gases emerge from the top of the reactor, normally via a tranquilization zone, also known as a velocity reduction zone, having a wider diameter than the fluidized bed and wherein fine particles entrained in the gas stream have an opportunity to gravitate back into the bed. It can also be advantageous to use a cyclone to remove ultra-fine particles from the hot gas stream. The gas is then normally recycled to the bed by means of a blower or compressor and one or more heat exchangers to strip the gas of the heat of polymerization.

A preferred method of cooling of the bed, in addition to the cooling provided by the cooled recycle gas, is to feed a volatile liquid to the bed to provide an evaporative cooling effect. The volatile liquid employed in this case can be, for example, a volatile inert liquid, for example, a saturated hydrocarbon having about 3 to about 8, preferably 4 to 6, carbon atoms. In the case that the monomer or comonomer itself is a volatile liquid, or can be condensed to provide such a liquid this can be suitably be fed to the bed to provide an evaporative cooling effect. Examples of olefin monomers which can be employed in this manner are olefins containing from about 3 to about eight, preferably from 3 to six carbon atoms. The volatile liquid evaporates in the hot fluidized bed to form gas which mixes with the fluidizing gas. If the volatile liquid is a monomer or comonomer, it will undergo some polymerization in the bed. The evaporated liquid then emerges from the reactor as part of the hot recycle gas, and enters the compression/heat exchange part of the recycle loop. The recycle gas is cooled in the heat exchanger and, if the temperature to which the gas is cooled is below the dew point, liquid will precipitate from the gas. This liquid is desirably recycled continuously to the fluidized bed. It is possible to recycle the precipitated liquid to the bed as liquid droplets carried in the recycle gas stream, as described, for example, in EP-A-89691, U.S. Pat. No. 4,543,399, WO 94/25495 and U.S. Pat. No. 5,352,749. A particularly preferred method of recycling the liquid to the bed is to separate the liquid from the recycle gas stream and to reinject this liquid directly into the bed, preferably using a method which generates fine droplets of the liquid within the bed. This type of process is described in WO 94/28032.

The polymerization reaction occurring in the gas fluidized bed is catalyzed by the continuous or semi-continuous addition of catalyst. Such catalyst can be supported on an inorganic or organic support material if desired. The catalyst can also be subjected to a prepolymerization step, for example, by polymerizing a small quantity of olefin monomer in a liquid inert diluent, to provide a catalyst composite comprising catalyst particles embedded in olefin polymer particles.

The polymer is produced directly in the fluidized bed by catalyzed (co)polymerization of the monomer(s) on the fluidized particles of catalyst, supported catalyst or prepolymer within the bed. Start-up of the polymerization reaction is achieved using a bed of preformed polymer particles, which, preferably, is similar to the target polyolefin, and conditioning the bed by drying with inert gas or nitrogen prior to introducing the catalyst, the monomer(s) and any other gases which it is desired to have in the recycle gas stream, such as a diluent gas, hydrogen chain transfer agent, or an inert condensable gas when operating in gas phase condensing mode. The produced polymer is discharged continuously or discontinuously from the fluidized bed as desired, optionally exposed to a catalyst kill and optionally pelletized.

Slurry polymerization conditions and supported catalyst preparation techniques for use therein are well known from the published literature. Generally such catalysts are prepared by the same techniques as are employed for making supported catalysts used in gas phase polymerizations. Slurry polymerization conditions generally encompass polymerization of a $C_{2-20}$ olefin, diolefin, cycloolefin, or mixture thereof in an aliphatic solvent at a temperature below that at which the polymer is readily soluble in the presence of a supported catalyst. Slurry phase processes particularly suited for the polymerization of $C_{2-6}$ olefins, especially the homopolymerization and copolymerization of ethylene and propylene, and the copolymerization of ethylene with $C_{3-8}$ α-olefins such as, for example, 1-butene, 1-hexene, 4-methyl-1-pentene and 1-octene are well known in the art. Such processes are used commercially on a large scale for the manufacture of high density polyethylene (HDPE), medium density polyethylene (MDPE), linear low density polyethylene (LLDPE) and polypropylene, especially isotactic polypropylene.

EXAMPLES

It is understood that the present invention is operable in the absence of any component which has not been specifically disclosed. The following examples are provided in order to further illustrate the invention and are not to be construed as limiting. Unless stated to the contrary, all parts and percentages are expressed on a weight basis. The term "overnight", if used, refers to a time of approximately 16–18 hours, "room temperature", if used, refers to a temperature of about 20–25° C., and "mixed alkanes" refers to a mixture of mostly $C_6$–$C_{12}$ alkanes available commercially under the trademark Isopar E™ from Exxon Chemicals Inc.

All manipulation of air sensitive materials was performed in an argon filled, vacuum atmospheres, glove box or on a high vacuum line using standard Shlenk techniques. Toluene was purified by passage through columns packed with activated alumina (Kaiser A-2) and supported copper (Engelhard, Cu-0224 S). Hexanes were purified by distillation from sodium benzophenone ketyl. Tris (pentafluorophenyl)borane was purchased from Boulder Scientific. Potassium azide was purchased from Atomergic Chemetals Corp., and used as received. Dioctadecylmethylamine is a bis(hydrogenated tallow) alkylamine of approximate formulation $(C_{18}H_{35})_2CH_3N$, available commercially under the tradename Armeen™ M2HT from Akzo Nobel, Inc., and was used as received.

Example 1

A) Synthesis of 2-(4-hydroxyphenyl)imidazole—
$HOC_6H_4C_3H_3N_2$

A flask was charged with 4-hydroxybenzaldehyde (30.0 g, 0.246 mol) and conc. ammonium hydroxide (36 mL). The solution was cooled to 0° C. and glyoxal (45 mL, 0.392 mol) was added dropwise via syringe over 30 minutes. A yellow precipitate formed and the slurry was stirred and allowed to warm to 25° C. for two hours. The product was collected on a frit, washed with cold water, and dried under reduced pressure to give a yellow powder (29.4 g, 75 percent yield). The solid was recrystallized from dimethylformamide (DMF) to give a tan powder.

$^1$H NMR (DMSO) δ12.23 (br s, 1H, N$\underline{H}$), 9.72 (br s, 1H, O$\underline{H}$), 7.74 (d, J=8.6 Hz, 2H, Ph), 7.04 (s, 2H, imidazole C$\underline{H}$=C$\underline{H}$), 6.81 (d, J=8.6 Hz, 2H, Ph). $^{13}$C NMR (DMSO) δ157.46 (Ph $\underline{C}$OH), 146.06 (Ph $\underline{C}$CN$_2$HCH$_2$), 132.17 ($\underline{C}$N$_2$HC$_{-2}$H$_2$),126.37 (Ph $\underline{C}$H), 122.26 (CN$_2$H$\underline{C}_2$H$_2$), 115.41 (Ph $\underline{C}$H). MS (M+H$^+$161.0).

B) Synthesis of 2-(4-trimethylsiloxyphenyl)imidazole— TMSOC$_6$H$_4$C$_3$H$_3$N$_2$ A flask was charged with the 2-(4-hydroxyphenyl) imidazole (1.00 g, 6.24 mmol) and 25 mL of CH$_2$Cl$_2$. To the slurry was added trimethylsilylchloride and triethylamine via syringe. The mixture clarified to give an amber solution. After stirring for 3 hours at 25° C., the volatiles were removed and the residue triturated once with hexanes and then dissolved in toluene. Filtration through diatomaceous earth filter aid and recrystallization from toluene yielded 0.914 g (63 percent yield) of the desired product as a tan solid.

$^1$H NMR (CH$_2$Cl$_2$) δ12.63 (s, 1H, N$\underline{H}$), 7.80 (d, J=8.5 Hz, 2H, Ph), 7.11 (s, 2H, imidazole C$\underline{H}$=C$\underline{H}$), 6.81 (d, J=8.5 Hz, 2H, Ph), 0.26 (s, 9H, Si$\underline{Me}_3$). $^{13}$C NMR (CH$_2$Cl$_2$) δ156.32 (Ph $\underline{C}$OSiMe$_3$), 147.74 (Ph $\underline{C}$CN$_2$HCH$_2$), 127.62 (Ph $\underline{C}$H), 124.70 ($\underline{C}$N$_2$HC$_2$H$_2$), 123.28 (CN$_2$H$\underline{C}_2$H$_2$), 120.89 (Ph $\underline{C}$H), 0.39 (SiMe$_3$). MS (M$^+$232.1).

C) Preparation of $[H(C_{18}H_{35})_2(CH_3)N]^+\{(HOC_6H_4C_3H_2N_2)[B(C_6F_5)_3]_2\}^-$ A vial was charged with 2-(4-hydroxyphenyl)imidazole (20.2 mg, 0.126 mmol), tris(pentafluorophenyl)borane (128.7 mg, 0.251 mmol), di(octadecyl)methylamine (66.8 mg, 0.128 mmol), and 2.0 mL of d$_8$-toluene. The mixture was stirred for 10 minutes until all of the solids dissolved and then analyzed to determine the product's identity.

$^1$H NMR (d$_8$-toluene) δ6.82 (br s, 1H, O$\underline{H}$), 6.47 (d, J=8.8 Hz, 2H, Ph), 6.85 (d, J=8.6 Hz, 2H, Ph), 5.85 (t, J=2.3 Hz, 2H, imidazole C$\underline{H}$=C$\underline{H}$), 4.07 (v br s, 1H, N$\underline{H}$), 2.24 (m, 2H, HNC$\underline{H}_2$), 2.05 (partially obscured m, 2H, HNC$\underline{H}_2$), 1.91 (d, J=5.1 Hz, 3H, N$\underline{Me}$), 1.4–1.0 (amine CH$_2$), 0.93 (t, J=6.7 Hz, 6H, N(CH$_2$)$_n$C$\underline{H}_3$). $^{19}$F NMR (d$_8$-toluene) δ o-C$\underline{F}$ [−127.29 ("d", 1F), −132.72 ("d", 1F), −133.45 & −133.75 (br m & "d"), 10F], p-C$\underline{F}$ [−156.66 (t, J=19.8 Hz, 1F), −159.09 (t, J=19.3 Hz, 2F), −160.79 (t, J=22.0 Hz, 3F)], m-C$\underline{F}$ [−162.96 ("br t", J=22.9 Hz, 1F), −163.64 ("br t", J=21.4 Hz, 1F), −165.78 & −166.12 (m & br m, 10F)]. MS cation [(M$^+$537.5) fragments 536.5, 509.5, 508.5 (base), 480.5)], anion {(M$^-$1182.6) fragments 872.7, 670.6 [base, (M-B (C$_6$F$_5$)$_3^-$)], 632.6}.

Example 2

Large Scale Preparation of [H(C$_{18}$H$_{35}$)$_2$(CH$_3$)N]$^+${(HOC$_6$H$_4$C$_3$H$_2$N$_2$)[B(C$_6$F$_5$)$_3$]$_2$}$^-$ A 250 mL flask was charged with 2-(4-hydroxyphenyl) imidazole (03.16 g, 1.97 mmol), tris(pentafluorophenyl) borane (2.02 g, 3.95 mmol), dioctadecylmethylamine (1.02 g, 1.96 mmol), and 100 mL of toluene. The mixture was stirred for 1 hour and then filtered through a frit. The volatiles were removed under reduced pressure to give a viscous, brown oil (3.10 g, 92.4 percent yield).

Example 3

Preparation of [H(C$_6$H$_5$)(CH$_3$)$_2$N]$^+${(Me$_3$SiOC$_6$H$_4$C$_3$H$_2$N$_2$)[B(C$_6$F$_5$)$_3$]$_2$}$^-$ A vial was charged with 2-(4-trimethylsiloxyphenyl) imidazole (20.4 mg, 0.088 mmol), tris(pentafluorophenyl) borane (90.0 mg, 0.176 mmol), ), dioctadecylmethylamine (47.0 mg, 0.090 mmol), and 2.0 mL of d$_8$-toluene. The cloudy mixture was stirred for 10 minutes until dissolved. The solution was analyzed for product identity.

$^1$H NMR (d$_8$-toluene) δ7.21 (br s, 2H, imidazole CH=CH), 6.65 (br d, J=7.8 Hz, 2H, Ph), 6.39 (d, J=8.8 Hz, 2H, Ph), 3.95 (v br s, 1H, N$\underline{H}$), 2.04 (br m, 4H, HNC$\underline{H}_2$), 1.77 (s, 3H, NM$\underline{e}$), 1.4–1.0 (amine CH$_2$), 0.93 (t, J=6.8 Hz, N(CH$_2$)$_n$C$\underline{H}_3$ overlaps with some amine resonances), 0.12 (s, 9H, SiM$\underline{e}_3$). $^{19}$F NMR (d$_8$-toluene) δ o-C$\underline{F}$ [−125.71 (br s, 2F), −132.5 & −132.43 (v br m & br s), 10F], p-C$\underline{F}$ [−157.85 (t, J=21.4 Hz, 2F), −160.28 (br "t", 4F)], m-C$\underline{F}$ [−163.78 ("br t", 2F), −164.37 (br s, 2F), −166.50 (v br s, 8F)]. MS cation [(M$^+$537.6) fragments 536.5, 509.6, 508.6 (base), 480.6)], anion {(M$^-$1254.8) fragments 742.6 [base, (M-B(C$_6$F$_5$)$_3^-$)]}.

Example 4

Preparation of [H(C$_{18}$H$_{35}$)$_2$(CH$_3$)N]$^+${(Me$_3$SiOC$_6$H$_4$C$_3$H$_2$N$_2$)[Al(C$_6$F$_5$)$_3$]$_2$}$^-$ A vial was charged with 2-(4-trimethylsiloxyphenyl) imidazole (20.5 mg, 0.088 mmol), tris(pentafluorophenyl) aluminane.½(toluene) (103.1 mg, 0.180 mmol), di(octadecyl)methylamine (46.0 mg, 0.088 mmol), and 2.0 mL of d$_8$-toluene. The mixture was stirred for 15 minutes until all of the solids dissolved and then analyzed.

$^1$H NMR (d$_8$-toluene) δ7.40 (s, 2H, imidazole CH=CH), 7.31 (d, J=8.5 Hz, 2H, Ph), 6.36 (d, J=8.6 Hz, 2H, Ph), 4.35 (v br s, 1H, N$\underline{H}$), 2.01 (br m, 4H, HNC$\underline{H}_2$), 1.73 (s, 3H, N M$\underline{e}$), 1.4–1.0 (amine CH$_2$), 0.93 (t, J=6.6 Hz, N(CH$_2$)$_n$C$\underline{H}_3$ overlaps with some amine resonances), 0.12 (s, 9H, SiM$\underline{e}_3$). $^{19}$F NMR (d$_8$-toluene) δ−121.79 (dd, J=27.4 & 18.3, 2F, o-C$\underline{F}$), −155.02 (t, J=19.8 Hz, 1F, p-C$\underline{F}$), −162.73 (m, 2F, m-C$\underline{F}$). MS cation [(M$^+$537.8) fragments 536.8, 509.8, 508.8, (base), 480.7], anion [M$^-$1286.9 (base)].

Example 5

Preparation of [H(C$_{18}$H$_{35}$)$_2$(CH$_3$)N]$^+${(Et$_2$AlOC$_6$H$_4$C$_3$H$_2$N$_2$)[B(C$_6$F$_5$)$_3$]$_2$}$^-$ (di(octadecyl) methylammonium 2-(4-diethylaluminoxyphenyl) imidazolate bis[tris(pentafluorophenyl)borane])

Under an argon atmosphere, a toluene solution of di(octadecyl)methyl-ammonium 2-(4-hydroxyphenyl) imidazolate bis[tris(pentafluorophenyl)borane] ([H(C$_{18}$H$_5$)$_2$(CH$_3$)N]$^+${(HOC$_6$H$_4$C$_3$H$_2$N$_2$)[B(C$_6$F$_5$)$_3$]$_2$}$^-$, 825 μl, 0.040M, 33.0 μmol) and a toluene solution of triethyl aluminum (363 μl, 0.10M, 36.3 μmol) were added to a vial and mixed for 30 seconds. Formation of the desired product can be identified by nuclear magnetic resonance spectroscopy.

Example 6a and 6b

Preparation of Supported Catalyst System

Di(octadecyl)methylammonium 2-(4-hydroxyphenyl)imidazolate bis[tris(pentafluorophenyl)borane] on TEA/silica Under an argon atmosphere, a toluene solution of di(octadecyl)methyl ammonium 2-(4-hydroxyphenyl) imidazolate bis[tris(pentafluorophenyl)borane] ([H(C$_{18}$H$_{35}$)$_2$(CH$_3$)N]$^+${(HOC$_6$H$_4$C$_3$H$_2$N$_2$)[B(C$_6$F$_5$)$_3$]$_2$}$^-$, 8.25 μl, 0.040M, 33.0 μmol) was diluted to 1500 μl with toluene and added to 1.00 g of triethylaluminum (TEA)-treated silica (Grace-Davison 948 silica, available from Grace-Davison Company, heated at 250° C. for 4 h, treated with 1.5 mmol TEA/g, washed with toluene and hexanes and dried under reduced pressure). The mixture was shaken by hand to break-up clumps and then mechanically agitated for 5 minutes. The volatiles were then removed under reduced pressure. A toluene solution of (t-butylamido)dimethyl (tetramethylcyclopentadienyl)silane titanium 1,3-pentadiene (1500 μl, 0.020M, 30.0 μmol) was added to the TEA-treated silica. The mixture was shaken by hand to break-up clumps and then mechanically agitated for 5 minutes. The volatiles were then removed under reduced pressure to give an olive green solid (0.988 g).

Example 7

Preparation of Supported Catalyst System

Di(octadecyl)methylammonium 2-(4-diethylaluminoxyphenyl)imidazolate bis[tris(pentafluorophenyl)borane] on TEA/silica Under an argon atmosphere, a toluene solution of di(octadecyl)methyl-ammonium 2-(4-hydroxyphenyl) imidazolate bis[tris(pentafluorophenyl)borane] (825 μl, 0.040M, 33.0 μmol) and a toluene solution of triethyl aluminum (363 μl, 0.10M, 36.3 μmol) were added to a vial and mixed for 30 seconds. This solution was then added to 1.00 g of TEA-treated silica (Grace-Davison 948, heated at 250° C. for 4 h, treated with 1.5 mmol TEA/g, washed with toluene and hexanes and dried under reduced pressure). The mixture was shaken by hand to break-up clumps and then mechanically agitated for 5 minutes. The volatiles were then removed under reduced pressure. A toluene solution of (t-butylamido)dimethyl(tetramethylcyclopentadienyl) silanetitanium 1,3-pentadiene (1500 μl, 0.020M, 30.0 μmol) was added to the silica. The mixture was shaken by hand to break-up clumps and then mechanically agitated for 5 minutes. The volatiles were then removed under reduced pressure to give the desired supported catalyst product as an olive green solid (1.00 g).

Example 8

Preparation of Supported Catalyst System

Di(octadecyl)methylammonium 2-(4-hydroxyphenyl)imidazolate bis[tris(pentafluorophenyl)borane] w/(EBI)Zr(DPB) on TEA/silica Under an argon atmosphere, a toluene solution of di(octadecyl)methyl ammonium 2-(4-hydroxyphenyl)

imidazolate bis[tris(pentafluorophenyl)borane] ([H(C$_{18}$H$_{35}$)$_2$(CH$_3$)N]$^+${(HOC$_6$H$_4$C$_3$H$_2$N$_2$)[B(C$_6$F$_5$)$_3$]$_2$}$^-$, 8.25 µl, 0.040M, 33.0 µmol) was diluted to 1500 µl with toluene and added to 1.00 g of triethylaluminum (TEA)-treated silica (Grace-Davison 948 silica, available from Grace-Davison Company heated at 250° C. for 4 h, treated with 1.5 mmol TEA/g, washed with toluene and hexanes and dried under reduced pressure). The mixture was shaken by hand to break-up clumps and then mechanically agitated for 5 minutes. The volatiles were then removed under reduced pressure. A toluene solution rac-ethylenebis(indenyl)zirconium (1,4-diphenylbutadiene) (1500 µl, 0.020M, 30.0 µmol) was added to the TEA-treated silica. The mixture was shaken by hand to break-up clumps and then mechanically agitated for 5 minutes. The volatiles were then removed under reduced pressure to give a purple-gray solid (1.061 g).

Example 9

Preparation of Supported Catalyst System

Di(octadecyl)methylammonium 2-(4-diethylaluminoxyphenyl)imidazolate bis[tris(pentafluorophenyl)borane] w/(EBI)Zr(DPB) on TEA/silica Under an argon atmosphere, a toluene solution of di(octadecyl)methyl-ammonium 2-(4-hydroxyphenyl)imidazolate bis[tris(pentafluorophenyl)borane] (825 µl, 0.040M, 33.0 µmol) and a toluene solution of triethyl aluminum (363 µl, 0.10M, 36.3 µmol) were added to a vial and mixed for 30 seconds. This solution was then added to 1.00 g of TEA-treated silica (Grace-Davison 948, heated at 250° C. for 4 h, treated with 1.5 mmol TEA/g, washed with toluene and hexanes and dried under reduced pressure). The mixture was shaken by hand to break-up clumps and then mechanically agitated for 5 minutes. The volatiles were then removed under reduced pressure. A toluene solution rac-ethylenebis(indenyl)zirconium(1,4-diphenylbutadiene) (1500 µl, 0.020M, 30.0 µmol) was added to the silica. The mixture was shaken by hand to break-up clumps and then mechanically agitated for 5 minutes. The volatiles were then removed under reduced pressure to give the desired supported catalysts product as a purple-gray solid (1.065 g).

Gas Phase Polymerizations

A 2.5-L stirred, fixed bed autoclave was charged with 200 g dry NaCl containing 0.1 g of KH as a scavenger. Stirring was begun at 300 rpm. The reactor was pressurized to 0.8 MPa ethylene and heated to 70° C. 1-hexene (7000 ppm) was introduced to the reactor followed by the addition of hydrogen (when used). In a separate vessel, 0.05 g of catalyst was mixed with an additional 0.1 g KH scavenger. The combined catalyst and scavenger were subsequently injected into the reactor. Ethylene pressure was maintained on demand while hexene and hydrogen (where used) were fed to the reactor to maintain their respective concentrations. The temperature of the reactor was regulated by a circulating water bath. After 90 minutes the reactor was depressurized, and the salt and polymer were removed. The polymer was washed with copious quantities of distilled water to remove the salt, dried at 60° C., and then stabilized by addition of a hindered phenol antioxidant (Irganox™ 1010 from Ciba Geigy Corporation) and 133 mg of a phosphorus stabilizer. Activity values were calculated based on ethylene uptake. Results are shown in Table 1.

TABLE 1

| Run | Catalyst | Co-catalyst | H$_2$ (ppm) | Activity (g/ghb)[3] | Density | I$_2$ | Mw |
|-----|----------|-------------|-------------|---------------------|---------|-------|--------|
| 1 | T$^1$ | Ex 6 | 2000 | 18.0 | 0.912 | 0.296 | 139,000 |
| 2 | E$^2$ | Ex 8 | 0 | 59.9 | 0.922 | <0.300 | 210,000 |
| 3 | " | " | 2000 | 36.7 | 0.92 | 1.017 | 92,500 |
| 4 | T$^1$ | Ex 7 | 2000 | 25.3 | 0.914 | 0.92 | 117,000 |
| 5 | E$^2$ | Ex 9 | 0 | 75.7 | 0.924 | <1.04 | 191,000 |
| 6 | " | " | 2000 | 47.8 | 0.927 | 3.22 | 110,000 |
| 7 | " | " | 0 | 64.3 | 0.924 | <1.233 | 193,000 |

[1](t-butylamido)dimethyl(tetramethylcyclopentadienyl)titanium 1,3-pentadiene
[2]ethylenebis(inden-1-yl)zirconium 1,4-diphenyl-1,3-butadiene
[3]grams polymer per gram (solid catalyst) · hour · (MPa × 0.1)

What is claimed is:
1. A compound corresponding to the formula:

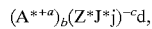

wherein:
A* is a cation of from 1 to 80 atoms, not counting hydrogen atoms, said A* having a charge +a,
Z* is an anion group of from 1 to 50 atoms, not counting hydrogen atoms, further containing two or more Lewis base sites;
J* independently each occurrence is a Lewis acid of from 1 to 80 atoms, not counting hydrogen atoms, coordinated to at least one Lewis base site of Z*, and optionally two or more such J* groups may be joined together in a moiety having multiple Lewis acidic functionality,
j is a number from 2 to 12 and
a, b, c, and d are integers from 1 to 3, with the proviso that a×b is equal to c×d, and provided further that one or more of A*, Z* or J* comprises a hydroxyl group or a polar group containing quiescent reactive functionality.

2. A compound according to claim 1 wherein A*$^{+a}$ is selected from the group consisting of ammonium, sulfonium, phosphonium, oxonium, carbonium, silylium, ferrocenium, Ag$^+$, and Pb$^{+2}$ cations.

3. The compound according to claim 1 wherein Z* is selected from the group consisting of trialkylsiloxy-, trialkylsiloxyalkyl-, trialkylsiloxyaryl-, and dialkylaluminoxyaryl-substituted derivatives of imidazolide, 2-(C$_{1-30}$hydrocarbyl)imidazolide, 4,5-dihaloimidazolide, 4,5-di(C$_{1-30}$hydrocarbyl)imidazolide, 2-(C$_{1-30}$hydrocarbyl)-4,5-benzimidazolide, and 5,6-dimethylbenzimidazolide.

4. The compound according to claim 1 which is an ammonium, phosphonium, sulfonium, oxonium carbonium, silylium, lead (II), silver or ferrocenium salt of hydroxylphenyl-, trimethylsiloxyphenyl-, and dialkylaluminoxyphenyl-substituted derivatives of:
bis(tris(pentafluorophenyl)borane)-imidazolide,
bis(tris(pentafluorophenyl)borane)-2-undecyl-imidazolide,
bis(tris(pentafluorophenyl)borane)-4,5-bis(heptadecyl)imidazolide,
bis(tris(pentafluorophenyl)aluman)imidazolide,
bis(tris(pentafluorophenyl)aluman-2-undecylimidazolide,
bis(tris(pentafluorophenyl)aluman-4,5-benzimidazolide, or
bis(tris(pentafluorophenyl)aluman-4,5-bis(heptadecyl)imidazolide.

5. A ammonium salt compound according to claim 1 wherein the ammonium cation is a trimethylammonium-, triethylammonium-, tripropylammonium-, tri(n-butyl) ammonium-, methyldi(octadecyl)ammonium-, methyldi(tetradecyl)ammonium-, methyl(tetradecyl)(octadecyl) ammonium-, N,N-dimethylanilinium-, N,N-diethylanilinium-, N,N-dimethyl(2,4,6-trimethylanilinium)-, N,N-di(tetradecyl)lanilinium-, N,N-di(tetradecyl)-2,4,6-trimethylanilinium)-, N,N-di(octadecyl)lanilinium-, N,N-di(octadecyl)-2,4,6-trimethylanilinium)-, or methyldicyclohexylammonium-cation.

6. The compound according to claim 1 corresponding to the formula:

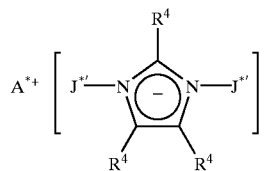

wherein:
A$^{*+}$ is a monovalent cation as previously defined in claim 1,
R$^4$, independently each occurrence, is hydrogen or a hydroxyhydrocarbyl, halo, hydrocarbyl, halocarbyl, halohydrocarbyl, silylhydrocarbyl, or silyl group, (including mono-, di- and tri(hydrocarbyl)silyl) group of up to 30 atoms not counting hydrogen, preferably C$_{1-20}$ alkyl group, or a quiescent reactive group, with the proviso that at least one R$^4$ group contains a hydroxyhydrocarbyl group or a quiescent reactive group, and
J* is tris(pentafluorophenyl)borane or tris(pentafluorophenyl)alumane).

7. The compound according to claim 1 that is a trihydrocarbylammonium-salt of:
bis(tris(pentafluorophenyl)borane)-2-(p-hydroxyphenyl)imidazolide,
bis(tris(pentafluorophenyl)borane)-2-undecyl-4-(p-hydroxyphenyl)imidazolide,
bis(tris(pentafluorophenyl)borane)-2-heptadecyl-4-(p-hydroxyphenyl)imidazolide,
bis(tris(pentafluorophenyl)borane)-2-(p-hydroxyphenyl)-4,5-bis(undecyl)imidazolide,
bis(tris(pentafluorophenyl)borane)-2-(p-hydroxyphenyl)-4,5-bis(heptadecyl)imidazolide;
bis(tris(pentafluorophenyl)borane)-2-(p-trimethylsiloxyphenyl)imidazolide,
bis(tris(pentafluorophenyl)borane)-2-undecyl-4-(p-trimethylsiloxyphenyl)imidazolide,
bis(tris(pentafluorophenyl)borane)-2-heptadecyl-4-(p-trimethylsiloxyphenyl)imidazolide,
bis(tris(pentafluorophenyl)borane)-2-(p-trimethylsiloxyphenyl)-4,5-bis(undecyl)imidazolide,
bis(tris(pentafluorophenyl)borane)-2-(p-trimethylsiloxyphenyl)-4,5-bis(heptadecyl)imidazolide;
bis(tris(pentafluorophenyl)borane)-2-(p-diethylaluminoxyphenyl)imidazolide,
bis(tris(pentafluorophenyl)borane)-2-undecyl-4-(p-diethylaluminoxyphenyl)imidazolide,
bis(tris(pentafluorophenyl)borane)-2-heptadecyl-4-(p-diethylaluminoxyphenyl)imidazolide,
bis(tris(pentafluorophenyl)borane)-2-(p-diethylaluminoxyphenyl)-4,5-bis(undecyl)imidazolide,
bis(tris(pentafluorophenyl)borane)-2-(p-diethylaluminoxyphenyl)-4,5-bis(heptadecyl)imidazolide;
bis(tris(pentafluorophenyl)alumane)-2-(p-hydroxyphenyl)imidazolide,
bis(tris(pentafluorophenyl)alumane)-2-undecyl-4-(p-hydroxyphenyl)imidazolide,
bis(tris(pentafluorophenyl)alumane)-2-heptadecyl-4-(p-hydroxyphenyl)imidazolide,
bis(tris(pentafluorophenyl)alumane)-2-(p-hydroxyphenyl)-4,5-bis(undecyl)imidazolide,
bis(tris(pentafluorophenyl)alumane)-2-(p-hydroxyphenyl)-4,5-bis(heptadecyl)imidazolide;
bis(tris(pentafluorophenyl)alumane)-2-(p-trimethylsiloxyphenyl)imidazolide,
bis(tris(pentafluorophenyl)alumane)-2-undecyl-4-(p-trimethylsiloxyphenyl)imidazolide,
bis(tris(pentafluorophenyl)alumane)-2-heptadecyl-4-(p-trimethylsiloxyphenyl)imidazolide,
bis(tris(pentafluorophenyl)alumane)-2-(p-trimethylsiloxyphenyl)-4,5-bis(undecyl)imidazolide,
bis(tris(pentafluorophenyl)alumane)-2-(p-trimethylsiloxyphenyl)-4,5-bis(heptadecyl)imidazolide;
bis(tris(pentafluorophenyl)alumane)-2-(p-diethylaluminoxyphenyl)imidazolide,
bis(tris(pentafluorophenyl)alumane)-2-undecyl-4-(p-diethylaluminoxyphenyl)imidazolide,
bis(tris(pentafluorophenyl)alumane)-2-heptadecyl-4-(p-diethylaluminoxyphenylyl)-imidazolide,
bis(tris(pentafluorophenyl)alumane)-2-(p-diethylaluminoxyphenyl)-4,5-bis(undecyl)imidazolide, or
bis(tris(pentafluorophenyl)alumane)-2-(p-diethylaluminoxyphenyl)-4,5-bis(heptadecyl)imidazolide.

8. The compound as recited in claim 1, wherein A* is a cation of from 1 to 60 atoms, not counting hydrogen atoms.

9. The compound as recited in claim 1, wherein Z* is an anion group of from 1 to 30 atoms, not counting hydrogen atoms.

10. The compound as recited in claim 1, wherein J* independently each occurrence is a Lewis acid of from 1 to 60 atoms, not counting hydrogen atoms.

* * * * *